US007968086B2

(12) United States Patent
Gromeier et al.

(10) Patent No.: US 7,968,086 B2
(45) Date of Patent: Jun. 28, 2011

(54) GENETICALLY STABLE ENTEROVIRUS EXPRESSION VECTOR WITH REPLACED STEM LOOP VI

(75) Inventors: Matthias Gromeier, Durham, NC (US); Elena Y. Dobrikova, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 10/304,059

(22) Filed: Nov. 26, 2002

(65) Prior Publication Data

US 2003/0158141 A1 Aug. 21, 2003

Related U.S. Application Data

(60) Provisional application No. 60/332,554, filed on Nov. 26, 2001.

(51) Int. Cl.
*A61K 48/00* (2006.01)
*A01N 63/00* (2006.01)
*C12N 15/00* (2006.01)

(52) U.S. Cl. .................... 424/93.2; 424/93.6; 435/320.1

(58) Field of Classification Search ................. 536/23.1, 536/24.1; 514/44; 424/93.1; 435/320.1; 800/8
See application file for complete search history.

(56) References Cited

U.S. PATENT DOCUMENTS

| | | | | |
|---|---|---|---|---|
| 5,738,985 | A | 4/1998 | Miles et al. | 435/5 |
| 5,955,318 | A | 9/1999 | Simons et al. | 435/71.1 |
| 6,156,496 | A | 12/2000 | Miles et al. | 435/5 |

OTHER PUBLICATIONS

Gromeier (1996) Proc. Natl. Acad. Sci., USA., 93: 2370-75.*
Deonarain (1998) Exp. Opin. Ther. Pat., 8(1): 53-69.*
Gorecki (2001) Exp. Opin. Emerging Drugs, 6(2): 187-98.*
Verma, et al. (1997) Nature, 389: 239-42.*
Eck, et al. (1996) Goodman & Gilman's The Pharmacological Basis of Therapeutics, 9th Ed., McGraw-Hill, New York, NY., pp. 77-101.*
Johansen, et al. (2000) Virology, 273: 391-99.*
Schnell, et al. (2001) FEMS Microbiol. Lett., 200: 123-29.*
Gromeier, et al. (1996) Prc. Natl. Acad. Sci., USA., 93: 2370-75.*
Tabernero, et al. (1997) J. Virol., 71(1): 95-101.*
Graff, et al. (1998) J. Virol., 72(5): 3571-77.*
Dobrikova, et al. (2003) Virol., 311: 241-53.*
Brown, et al. (1994) Journal of Virology, 68(2): 1066-74.*
Dufresne et al, "Genetically Stable Picornavirus Expression Vectors with Recombinant Internal Ribosomal Entry Sites", Journal of Virology 76(17):8966-8972 (2002).
Andino et al, "Engineering Poliovirus as a Vaccine Vector for the Expression of Diverse Antigens", Science 265:1448-1451 (1994).
Dobrikova et al, "Structural determinants of insert retention of poliovirus expression vectors with recombinant IRES elements", Virology 311:241-253 (2003).

* cited by examiner

*Primary Examiner* — Robert M Kelly
(74) *Attorney, Agent, or Firm* — Nixon & Vanderhye, PC

(57) ABSTRACT

The present invention relates, in general, to an expression vector and in particular, to a genetically stable viral expression vector.

11 Claims, 22 Drawing Sheets

5'
3'
Poliovirus
P1
P2
P3

Capsid Modification
P1
P2
P3

P1
2Apro
P2
P3

Dicistronic Expression Vectors
P1
P2
P3

I
5'
110
cloverleaf
II
III
IV
V
IRES
VI
Y(n) X(m)
aug
HRV
585
aug
743
PV
ORF

The Y(n)X(m)AUG motif
Deleting stem-loop domain VI
Y(n)
X(m)
uguuucacuuuuucccuuuauauuugc
uguuucacuuuuucccuuuagaucuaccaug
BglII
ORF
ORF

RP86

RPδ6-FimH
2Apro
PV-ORF
1 kB
0.5kB
M P T 1 2 3 4 5 6 20

RPδ6-HIVtat
1 kB
0.5kB
M P T 1 2 3 4 5 6 20

RPδ6-SIVp17
M P T 1 2 3 4 5 6 7 8 9 10 11 12 13 14 15 M
1 kB
0.5kB

RPδ6-EGFP
1 kB
0.5kB
M P T 1 2 3 4 5 6 RPδ6

RPδ6-$SIV_{p17}$-aag

RPδ6-$SIV_{p17}$-acc

RPδ6-HIV$_{tat}$(1) (ΔG=-26.9)

RPδ6-HIV$_{tat}$(2) (ΔG=-8.0)

RP86-HIVtat(3) (ΔG=-6.5)

Figure 14A

CPV A27L

```
         M  D  G  T   L  F  P  G  D  D   D  L  A  I   D  A  T   E  F  F   S  T  K  A   A  .  .   .
gtactttaa tggacggaac tcttttcccc ggagatgacg atcttgcaat tccagcgact gaatttttct ctacaaaggc tgctaagaag ccagaggcta aacgcgaagc aattgttaaa gctgagggag

atgacaatga agaaactctc aaacaacgac taactaattt ggaaaaaaag attactaatg taacaacaaa gtttgaacaa atcgaaaagt gttgtaaacg caacgatgaa gttctattta ggttggaaaa
  .  .  .   T  L  R   A  A  M  I   S  L  A   K  K  I   D  V  Q  T   G  R  R   P  Y  E
tcatgctgaa actctaagag cggctatgat atctctggct aaaaagattg atgttcagac tggacggcga ccatatgaat aaactcaact cttttgttt
```

Figure 14B

CAV21-CPV-A27L

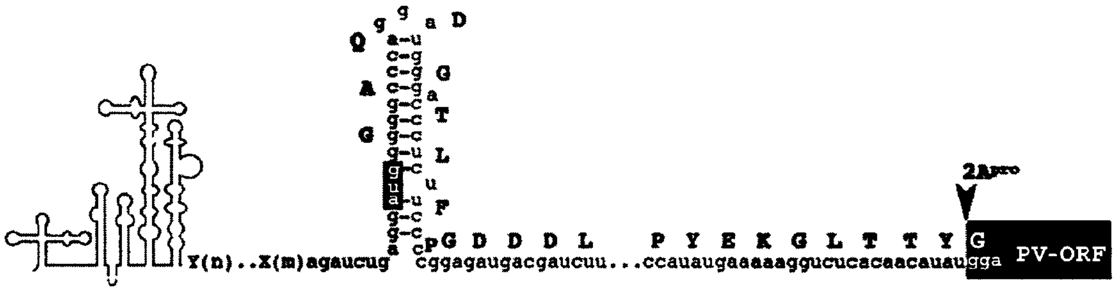

Figure 14C

CAV21-CPV-A27LΔ20

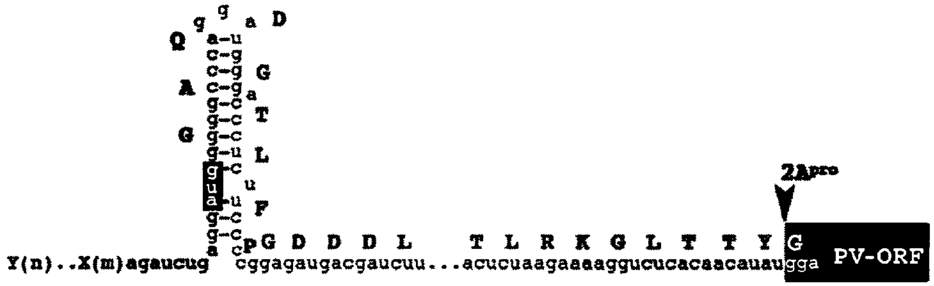

Figure 14D

CPV B5R

```
                                                                                               C    T   V   P   T   M   N  N    A   K  L    .   .   .
aacactcata aataaaatg aaaacgattt ccgttgttac gttgttatgc gtactacctg ctgttgttta ttcaacatgt actgtaccca ctatgaataa cgctaaatta acgtctaccg aaacatcgtt
                                                                                                                .   .    .  N   P   C
taatgataaa cagaaagtta cgtttacatg tgattcggga tattattctt tggatccaaa tgctgtctgt gaaacagata aatggacata cgaaaatcca tgcaagaaaa tgtgcacagt ttctgattat
gtctctgaac tatatgataa accgctatac gaagtgaatt .(n=668)ta a.........
```

Figure 14E

CAV21-CPV-B5R

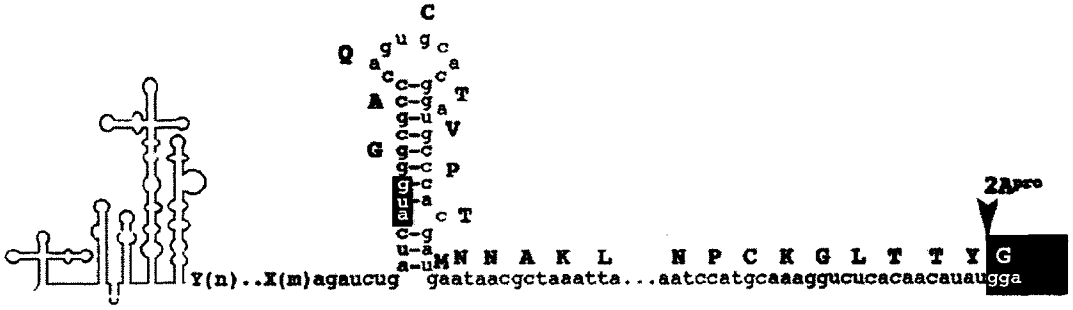

GENETICALLY STABLE ENTEROVIRUS EXPRESSION VECTOR WITH REPLACED STEM LOOP VI

This application claims priority from Provisional Application No. 60/332,554, filed Nov. 26, 2001, the content of which is incorporated herein by reference.

TECHNICAL FIELD

The present invention relates, in general, to an expression vector and, in particular, to a genetically stable viral expression vector and to methods of using same.

BACKGROUND

Live attenuated viruses were the first immunization agents available for protection against viral infection. Eradication of smallpox has been achieved through widespread immunization with vaccinia virus and a similar success with poliomyelitis may be imminent through the use of the live attenuated Sabin vaccine strains.

The live attenuated vaccine strains of poliovirus were the result of serial passages in cultured cells derived from a variety of hosts (Gromeier et al, Proc. Natl. Acad. Sci. USA 93:2370-2375 (1996)). Elucidation of the genetic basis of attenuation of poliovirus neurovirulence and a better understanding of the pathogenesis of poliomyelitis have opened the possibility to derive attenuated poliovirus variants through genetic engineering (Agol et al, J. Biotechnol. 44:119-128 (1996), Almond et al, Dev. Biol. Stand. 78:161-169 (1993), Gromeier et al, Proc. Natl. Acad. Sci. USA 93:2370-2375 (1996)). Attempts to construct live attenuated polioviruses were not limited to agents for the prophylaxis of poliomyelitis. Rather, the advantageous properties of live attenuated polioviruses have inspired investigations into possible uses as immunization vectors against infectious disease other than poliomyelitis (Andino et al, Science 265:1448-1451 (1994)).

Various strategies have been employed to engineer picornavirus-based expression vectors (FIG. 1). Insertion of peptide sequences into the coding region for the viral capsid proteins was designed to display foreign immunogenic peptides on the viral capsid exterior (FIG. 1B; Arnold et al, Intervirology 39:72-78 (1996)). Dicistronic vectors were generated through insertion of foreign sequences under translational control of a secondary, heterologous IRES element inserted in between P1 and P2 (FIG. 1C) or at the N-terminus of the polyprotein (Alexander et al, Proc. Natl. Acad. Sci. USA 91:1406-1410 (1994)); FIG. 1D). Similarly, polyprotein fusion vectors were created by inserting foreign ORFs (open reading frames) into similar positions, either separating P1 from P2, or through N-terminal fusion (FIGS. 1E, 1F). Finally, poliovirus replicons were generated by replacing the coding region for the capsid proteins (P1) with a heterologous ORF (FIG. 1G).

The size of foreign gene products to be expressed varied with the strategy chosen. Minimal insertions consisting of few amino acids within the capsid (FIG. 1B) and maximum ORFs coding for gene products up to 440 amino acids in length (FIG. 1E, 1F) constitute the range of permissible insertions. It is believed that this size constraint is largely a reflection of the limited ability of the compact picornaviral capsid to accommodate genomic RNAs containing added sequences (Alexander et al, Proc. Natl. Acad. Sci. USA 91:1406-1410 (1994), Andino et al, Science 265:1448-1451 (1994)).

A major obstacle common to all proposed replicating picornavirus expression vectors is their inherent genetic instability. Picornaviruses, due to the high error rate of their RNA-dependent RNA polymerase, replicate "at the threshold of error catastrophe" (Eigen et al, RNA Genetics, eds. Domingo et al, CRC, Boca Raton, Fla., pps. 211-245 (1988)). High mutation rates create a delicate balance between beneficial rapid adaptation to changing growth environments and the limits of genetic variability imposing loss of viability. Picornaviruses evolved to maintain this balance by limiting the size of their genome (approximately 7,500 bp; Kitamura et al, Nature 291:547-553)), highly productive genome replication, and through intra- and intergenomic recombination (Wimmer et al, Ann. Rev. Genet. 27:353-436 (1993)).

Differences in the structural context and insertion locale of foreign open reading frames can have profound influences on virus propagation efficiency and, thus, expression of inserted sequences. However, irrespective of their genetic structure, all proposed expression vectors share the inherent tendency to revert to wild-type sequences with maximal propagation potential. This tendency may be due to the deleterious effect of insertion of foreign sequences on virus replication efficiency, triggering events to adapt to a faster growing phenotype. These events will invariably lead to the elimination of all or parts of the inserted foreign sequences. This has been thoroughly documented for poliovirus polyprotein fusion expression vectors (see FIG. 1F; Mueller et al, J. Virol. 72:20-31 (1998)). It was proposed that homologous recombination events lead to very rapid elimination of inserted sequences within few replicative cycles (Mueller et al, J. Virol. 72:20-31 (1998)). Frequently, the presence of minimal truncated remnants of the insert could be demonstrated for extended numbers of passages (Mueller et al, J. Virol. 72:20-31 (1998)).

Genetic instability of viral expression vectors (particularly picornavirus expression vectors) greatly limits their usefulness for vaccination purposes. Rapid deletion of inserted foreign ORFs upon virus replication diminishes expression of the immunogen. Deletion events in attenuated expression constructs can also give rise to variants displaying pathogenic properties. Genetically unstable expression vectors can be difficult to propagate on a large scale and the verification of the genotype of produced stock is a major challenge, due to the heterogeneous mixture of deletion variants generated.

The present invention results from the development of a novel strategy for engineering viral-based expression vectors, particularly picornavirus-based expression vectors. This strategy is based principally on the concept of forcing viruses to retain foreign encoding sequences by substituting the foreign sequences for regulatory sequences in a manner such that the regulatory function is retained.

SUMMARY OF THE INVENTION

The present invention relates generally to genetically stable expression vectors. More specifically, the invention relates to genetically stable picornavirus expression vectors and to methods of using such vectors in immunization and gene therapy regimens.

Objects and advantages of the present invention will be clear from the description that follows.

BRIEF DESCRIPTION OF THE DRAWINGS

FIG. 1A. Poliovirus. FIG. 1B. Capsid inserts displayed on the particle exterior (Arnold et al, Intervirology 39:72-78 (1996)). FIG. 1C. Dicistronic vector with insert between P1 and P2 (Alexander et al, Proc. Natl. Acad. Sci. USA 91:1406-1410 (1992)). FIG. 1D. Dicistronic vector with insert between two tandem IRES elements (Alexander et al, Proc. Natl. Acad. Sci. USA 91:1406-1410 (1992)). FIG. 1E. Polyprotein fusion vector with insert between P1 and P2 (Crotty et al, J. Virol. 75:7435-7452 (2001)). FIG. 1F. Polyprotein fusion vector with N-terminal insert (Andino et al, Science 265:1448-1451 (1994)). FIG. 1G. Poliovirus replicon (Morrow et al, AIDS Res. Hum. Retroviruses 10:S61-66 (1994)). Heterologous sequences encoding foreign gene products are shown as hatched boxes. Proteolytic cleavage sites needed for the proteolytic release of fusion inserts by viral proteinases $2A^{pro}$ and $3C^{pro}$, respectively, are indicated. The predicted secondary structures of the poliovirus IRES (all constructs) and the IRES of encephalomyocarditis virus (EMCV; dicistronic constructs C and D) are shown.

FIG. 2A. Position and structure of the Y(n) X(m)AUG motif within the entero-/rhinovirus IRES. The locations of initiating AUGs of rhinovirus (HRV) and poliovirus (PV) are indicated by open boxes. Solid boxes represent non-initiating AUGs. Roman numerals atop refer to individual 5'NTR domains. FIG. 2B. Nucleotide sequence of the Y(n)X(m)AUG motif in the intact HRV2 IRES and in a stem-loop domain VI deletion mutant (SEQ ID NO:39 and SEQ ID NO:40, respectively). The sequence of X(m) was altered to insert a BglII endonuclease restriction site for cloning purposes and to put the adjacent AUG into Kozak context (cuu augu to accaugg; shown in gray italics). Y(n)X(m)AUG initiates translation of the polyprotein in the PVS-δ6 deletion construct. FIG. 2C. Genetic structure and growth characteristics of PVS-δ6. HRV2 IRES sequences are shown in gray. The construct gave rise to viable virus that grew with wild-type efficiently in HeLa cells and retained the neuron-specific replication defect of full-length PVS-RIPO in Sk-N-Mc neuroblastoma cells (Gromeier et al, Proc. Natl. Acad. Sci. USA 93:2370-2375 (1996)).

FIG. 3A. Genetic structure of a PVS-δ6/FimH expression construct (SEQ ID NO:41 and SEQ ID NO:43). FimH sequences are predicted to form a stable stem-loop structure in a position similar to stem-loop domain VI in the HRV2 IRES. An engineered $2A^{pro}$ cleavage site assures proper proteolytic processing of the fusion polyprotein. Amino acid sequence of the engineered proteolytic cleavage site is indicated atop the nucleotide sequence (SEQ ID NO:42). FIG. 2B. RT-PCR analyses of serially passaged expression construct. Retention of added sequences is observed after 15 passages. For comparison, PCR analysis of the "empty" PVS-δ6 cDNA is shown (far right lane).

FIG. 4A. Sequence and proposed secondary structure of the SIV AUG stem loop (Berkhout, Progr. Nucl. Acid Res. Mol. Biol. 54:1-34 (1996)) (SEQ ID NO:44). The initiating AUG of SIV-gag (boxed in black) is in a similar position to Y(n)X(m)AUG in the HRV2 IRES, forming the base of stem loop domain VI (compare with FIG. 2B) (SEQ ID NO:45). FIG. 4B. This general structural arrangement was maintained in the PVS-δ6/SIV-p17 expression vector, exchanging stem loop domain VI of the HRV2 IRES with the SIV AUG stem loop and inserting downstream SIV-p17 sequences (approx. 540 nt). The SIV AUG stem loop was altered to accommodate the poliovirus polyprotein signal peptide (MGAQ) without changing its predicted overall structure. Changed nucleotides are shown in bold and underlined. (SEQ ID NO:46 and SEQ ID NO:1) Amino acid residues are indicated adjacent to nucleotide sequences. (SEQ ID NO:47) As with stem loop domain VI deletion mutants, usage of Y(n)X(n)AUG as initiation site was achieved by creating a Kozak context (gagaugg to aagaugg). FIG. 4C. RT-PCR analysis of serial passages of PVS-δ6/SIV-p17. Black arrowheads indicate the expected size of the full length insert, red and blue arrowheads indicate deletion fragments emerging after 8 passages. The right panel depicts the results of sequencing analysis of the three predominant fragments amplified after 12 passages of PVS-δ6/SIV-p17. FIG. 4D. Genetic structure of a SIV-p17 expression construct containing the entire IRES of HRV2 (SEQ ID NO:2). This vector uses the authentic initiating AUG of the HRV2 IRES to drive translation of SIV-p17. (SEQ ID NO:3) The 3' structure was identical to PVS-δ6/SIV-p17, featuring a $2A^{pro}$ cleavage site. FIG. 4E. RT-PCR analysis of serially passaged vector. Confirming previously reported studies (Mueller et al, J. Virol. 72:20-31 (1998)), full length IRES constructs rapidly lost insert sequences upon replication in HeLa cells. After the $2^{nd}$ passage, a deletion variant supervened; after the $3^{rd}$ passage, no evidence for the presence of replicating full-length expression construct can be detected. For comparison, PCR amplification of full-length SIV-p17 from the corresponding cDNA is shown (lane P).

FIG. 5A. Genetic structure of PVS-δ6/SIV-p17 with the initiating AUG in accaugg context (SEQ ID NO:4). Note the different predicted stability of the AUG-domain, compared to PVS-δ6/SIV-p17 in aagaugg context (see FIG. 4B). (SEQ ID NO:47). FIG. 5B. Results of RT-PCR analyses of passaged virus. Clone #5 exhibited genetic instability identical to full-length IRES fusion polyprotein vectors (compare with FIG. 4E). Two passages after transfection, a deletion variant emerged and full-length SIV-p17 containing vector could no longer be detected. FIG. 5C. In contrast, after 2 passages, clone #6 evolved with enlarged insert size. Arrows point toward the fragment corresponding to full-length SIV-p17 (lane P=plasmid DNA), and the slightly enlarged PCR product. FIG. 5D. Sequencing of the enlarged insert fragment yielded the genetic structure shown (SEQ ID NO:5). The enlarged IRES/insert fragment features an exact duplication of the Y(n)X(m)AUG motif and the synthetic AUG stem-loop domain with the second AUG in frame in optimal Kozak context.

FIG. 7A. Genetic structure of PVS-RIPO. The HRV2 IRES is boxed in gray. The sequence detail depicts the domain structure of the IRES (roman numerals atop) and sequence of the polypyrimidine tract [Y(n)], spacer [(X(m)] and the cryptic AUG (asterisks) (SEQ ID NO:6). The HRV2 initiation codon is shown in bold, the ORF for the viral polyprotein as a black box. FIG. 7B. Genetic structure of RPδ6. SLD VI was deleted (δVI) and the cryptic AUG within Y(n)X(m)AUG was placed into Kozak context (SEQ ID NO:7). FIG. 7C. One-step growth curves of PVS-RIPO (diamonds) and RPδ6 (squares) in HeLa cells.

FIG. 9A. A SIV-p17 expression construct based on RPδ6, replacing the HRV2 IRES SLD VI with foreign sequences (SEQ ID NO:14 and SEQ ID NO:10) (SEQ ID NO:9) (see FIG. 8C; Dufresne et al, J. Virol. 76:8966-8972 (2002)). FIG. 9B. A SIV-p17 expression construct based on PVS-RIPO, containing the entire HRV2 IRES and using the authentic initiation codon of PVS-RIPO for translation of the fusion polyprotein (SEQ ID NO:15 and SEQ ID NO:10). Labeling is as shown in FIG. 8. The right hand panel depicts the results of RT-PCR analysis of serial passages of both constructs. Arrowheads indicate the endpoint deletion variants emerging after serial passaging of both constructs.

FIG. 10B. Western blot analysis of $SIV_{p17}$ expression by (FIG. 10A). In cells infected with (FIG. 10C (SEQ ID NO: 16)), expression of $SIV_{p17}$ could not be detected in any passage.

FIG. 11A (SEQ ID NO:11), FIG. 11B. The artificial SLDs within RPδ6-$HIV_{tat}$ (1) and -(2) have free energies of −26.9 kcal/mol and −8.0 kcal/mol, respectively (determined as described in Zuker et al, Algorithms and thermodynamics for RNA secondary structure prediction: a practical guide, p. 11-43, In Barciszewski and Clark (eds.), RNA Biochemistry and Biotechnology, Kluwer Academic Publishers: Amsterdam (1999)) (SEQ ID NO:17). FIG. 11C. Western blot detection of $HIV_{tat}$ throughout 20 passages of RPδ6-$HIV_{tat}$ (2). FIG. 11D. The free energy of artificial SLD within RPδ6-$HIV_{tat}$ (3) was reduced to −6.5 kcal/mol, leading to deletion events upon serial passages (SEQ ID NO:18). FIG. 11E. Genetic structure of a dominant deletion variant emerging after 3 passages of RPδ6-$HIV_{tat}$ (3) (FIG. 11D; red arrowhead) (SEQ ID NO:19). FIG. 11F. Genetic structure of an enlarged variant of RPδ6-$HIV_{tat}$ (3) emerging after passage 10 (FIG. 11D; green arrowhead) and evolving as the preponderant population after passage 14 (FIG. 11D) (SEQ ID NO:20 and SEQ ID NO:21). The insert of 129 nt acquired by replicating RPδ6-$HIV_{tat}$ (3) (green box) corresponded in sequence to a portion of the coding region for the VP2 capsid protein.

FIGS. 14A-14E. FIG. 14A. Sequence of the CPV A27L gene (SEQ ID NO:24). Initiation and termination codons are outlined by a black box. Sequences to be inserted into the CAV21 genome are shown in blue [either the entire ORF (FIG. 14B), or a deletion product lacking a C-terminal portion (gray shaded box) (FIG. 14C) will be inserted into CAV21]. Amino acid sequences are shown in capital letters (SEQ ID NO:25 and SEQ ID NO:26). FIG. 14B. Genetic structure of CAV21-CPV-A27L (SEQ ID NO:27 and SEQ ID NO:29) (SEQ ID NO:28 and SEQ ID NO:30), a recombinant CAV21 expression vector containing the CPV A27L ORF (blue). FIG. 14C. Genetic structure of CAV21-CPV-A27A20 (SEQ ID NO:27 and SEQ ID NO:31) (SEQ ID NO:28 and SEQ ID NO:32), encoding for a A27L deletion variant. FIG. 14D. Partial sequence of the CPV B5R gene (SEQ ID NO:33) (SEQ ID NO:34). Labeling is as described for (FIG. 14A). Insert sequences are shown in blue. FIG. 14E. Genetic structure of CAV21-CPV-B5R (SEQ ID NO:35 and SEQ ID NO:37), a recombinant CAV21 expression vector containing parts of the CPV B5R ORF frame known to contain critical antigenic epitopes (SEQ ID NO:36 and SEQ ID NO:37).

DETAILED DESCRIPTION OF THE INVENTION

The present invention relates to a new strategy for designing genetically stable viral expression vectors suitable for use in immunization and gene therapy regimens. This strategy takes advantage of the architecture of non-coding regulatory elements in the viral genome. In accordance with this strategy, a virus is coerced into retaining foreign (heterologous) inserted genetic material by replacing a regulatory secondary structure of the virus with a foreign encoding sequence having a comparable structure. The present strategy thus results in the creation of sequences that serve two functions: they exerted regulatory influences (due to secondary structure) and they encode a desired gene product.

The genetically stable expression vectors of the invention can be of a wide variety of viral types (e.g., Hepatitis C and picornaviruses). In a preferred embodiment, the present invention relates to a genetically stable picornavirus expression vector, for example, an enterovirus, poliovirus, foot and mouth disease virus, echovirus or Hepatitis A virus expression vector. The particular virus can be selected based, for example, on the foreign protein product to be expressed, the route by which the virus is to be administered and the nature of the effect sought. In accordance with this embodiment, a regulatory region of the picornavirus, the function of which is dependent upon secondary structure rather than primary structure, is replaced with a sequence coding for a foreign gene product having a secondary structure such that the regulatory function of the replaced sequence is maintained. That is, the coding sequence mimics (at least functionally) the general architecture of the structure for which it is substituted. As shown in the Example that follows, superb retention of foreign sequences within stem-loop domain VI IRES-deletion mutants is observed. Other IRES-deletion mutants can also be used, including, for example, stem-loop domain II, III, IV and V IRES-deletion mutants. It will be appreciated the presented strategy can be adapted for use both in viruses that naturally comprises an IRES and viruses engineered to comprise an IRES.

Figure 6B:
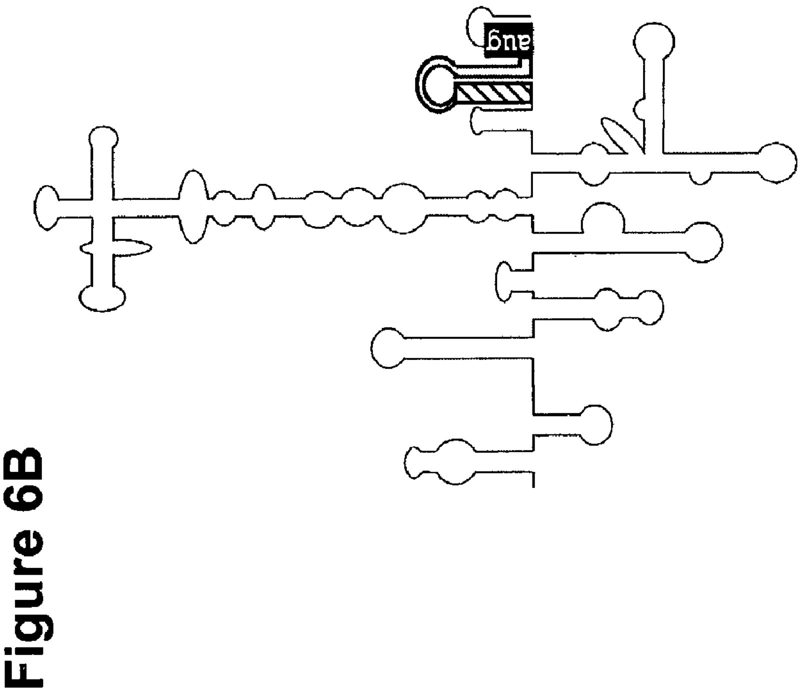
FIGS. 6A and 6B. Genetic structure and position of the Y(n)X(m)AUG motif in type 1 (FIG. 6A) and type 2 (FIG. 6B) IRESes. Y(n) is represented by a gray-, X(m) by an open- and AUG by a black box. The initiating AUG codon is shown. Type 1 IRESes initiate translation from an AUG triplet upstream the Y(n)X(m)AUG motif (at the base of stem-loop domain VI in rhinoviruses, downstream a 132 nt spacer in enteroviruses). Type 2 IRESes use Y(n)X(m)AUG for initiation.
Figure 6A:
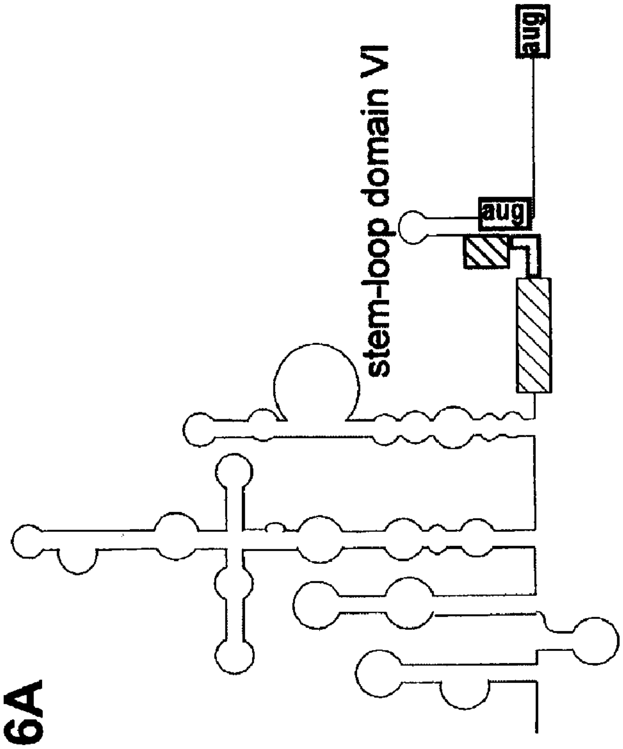

Picornavirus IRESes have been divided into type 1 (entero-, rhinoviruses) and type 2 (cardio-, aphthoviruses; Wimmer et al, Ann. Rev. Genet. 27:353-436 (1993)). Both, type 1 and 2 IRESes feature a highly conserved pyrimidine-rich tract [Y(n)] followed by a 15-20 nt spacer [X(m)] and an AUG triplet [the Y(n)X(m)AUG motif; FIG. 6]. The AUG triplet within Y(n)X(m)AUG serves as initiation codon in type 2-, but is cryptic in type 1 IRESes. In the latter, initiation of translation occurs from an AUG codon 19-154 nt downstream from Y(n)X(m)AUG (FIG. 6). Both, nucleotide sequence and distance between individual elements of the Y(n)X(m)AUG motif have been found crucial for proper IRES function (Pestova et al, Virology 204:729-737 (1994)).

Amongst type 1 IRESes the distance between Y(n)X(m) AUG and the initiation codon is variable. Both rhino- and enteroviruses feature a predicted stem-loop structure (domain VI; FIG. 6) formed by 3' terminal IRES sequences. In rhinoviruses, the initiation codon is part of the base of stem-loop domain VI, while in enteroviruses a poorly conserved spacer of 115-136 nt length separates stem-loop domain VI from the initiation codon (FIG. 6). This spacer is not essential for IRES function, since its deletion did not significantly reduce virus growth rate or IRES function (Iizuka et al, J. Virol. 63:5354-5363 (1989), Kuge et al, J. Virol. 61:1478-1487 (1987), Philipenko et al, Nucleic Acids Res. 18:3371-3375 (1990)). Similarly, deletion of stem-loop VI and shift of translation initiation to Y(n)X(m)AUG in polio- (Pestova et al, Virology 204:729-737 (1994)) or rhinovirus did not lead to loss of virus viability. These observations indicate that, like in type 2 IRESes, the Y(n)X(m)AUG motif can supply the initiation codon in entero- or rhinoviruses. However, since Y(n)X(m)AUG is never used for initiation in type 1 IRESes and because all entero- and rhinoviruses feature a conserved stem-loop domain VI (plus an added spacer in enteroviruses), these structural element must confer an advantage to the virus.

The present expression vectors can constructed such that a precursor product is expressed that comprises a signal peptide N-terminal to the desired foreign polypeptide and a cleavage site recognized by a viral or cellular protease that cleaves the foreign polypeptide from the viral polyprotein (see, for example, U.S. Pat. No. 5,965,124).

The expression vectors of the present invention can be used therapeutically and prophylactically to produce strong and sustained immune responses against antigens they encode. For example, the vectors can be engineered to express foreign polypeptides to induce immunity against infections, for example, bacterial, viral or fungal infections (e.g., HIV, hepatitis B), parasitic diseases, allergies or malignant (e.g., malignant melanoma) disease. (See also exogenous nucleic acid sequences described in U.S. Pat. No. 5,965,124.)

In addition to their usefulness in immunization, the expression vectors of the invention can also be used in gene therapy regimens.

The expression vectors of the invention are advantageously formulated with pharmaceutically acceptable diluants or carriers. Optimal dosing regiments can be readily established by one skilled in the art and will depend, for example, on the nature of the encoded antigen, the patient and the effect sought.

It will be appreciated that the expression vectors of the invention can also be used to produce encoded foreign polypeptides in tissue culture and that the polypeptide can be isolated from the cells and virus.

Certain aspects of the invention can be described in greater detail in the non-limiting Examples that follows.

EXAMPLE I

Genetically Stable Picornavirus Expression Vectors

The insertion of the IRES of human rhinovirus type 2 (HRV2) was previously shown to eliminate inherent neurovirulence of poliovirus (Gromeier et al, Proc. Natl. Acad. Sci. USA 93:2370-2375 (1996)). Because of its very favorable attenuation phenotype, the chimeric construct PVS-RIPO [featuring the genome of poliovirus (Sabin) serotype 1 containing the HRV2 IRES] has been used for the construction of expression constructs.

Figures 2A, 2B:
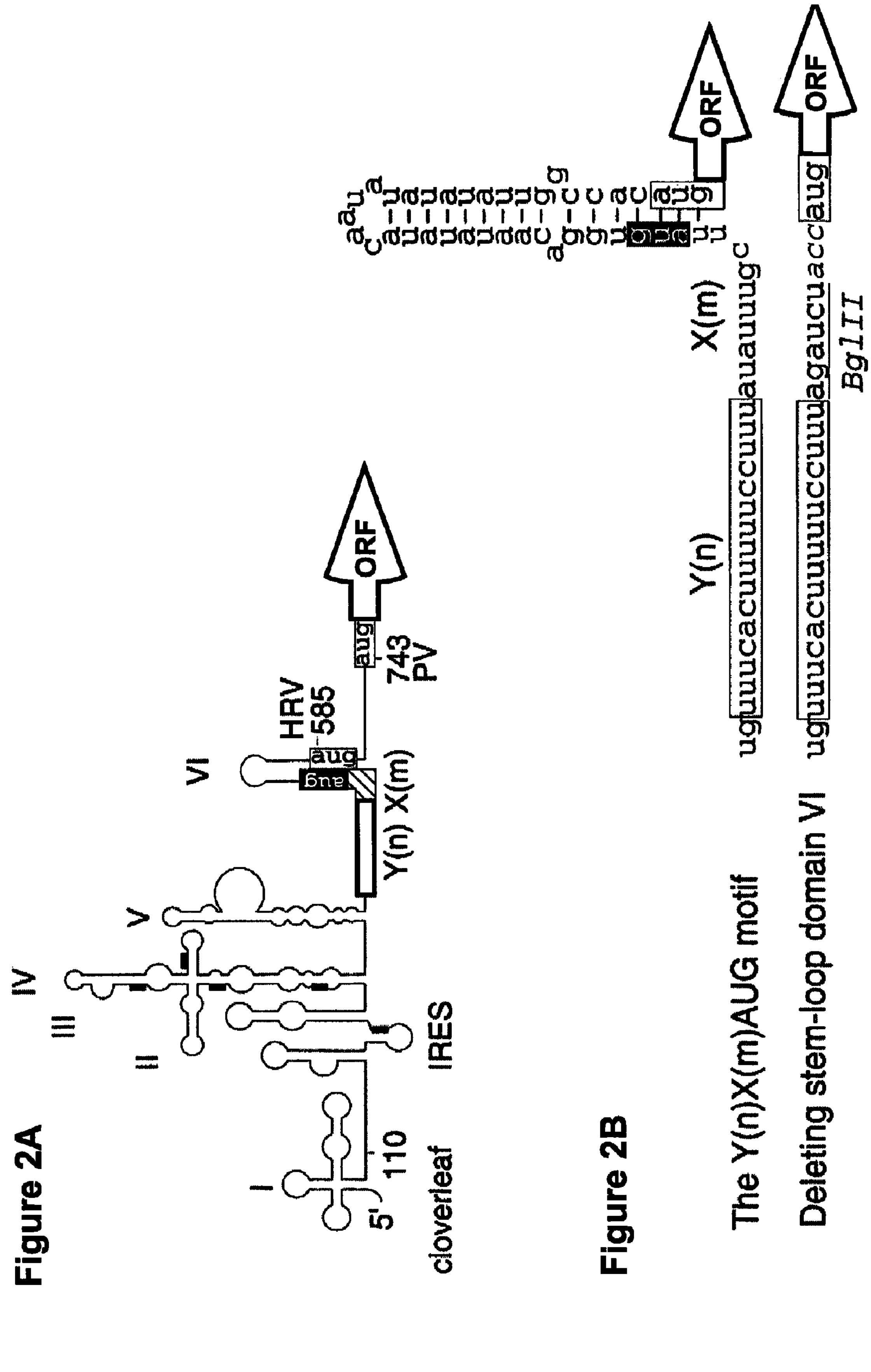
FIGS. 2A-2C.
Figure 2C:
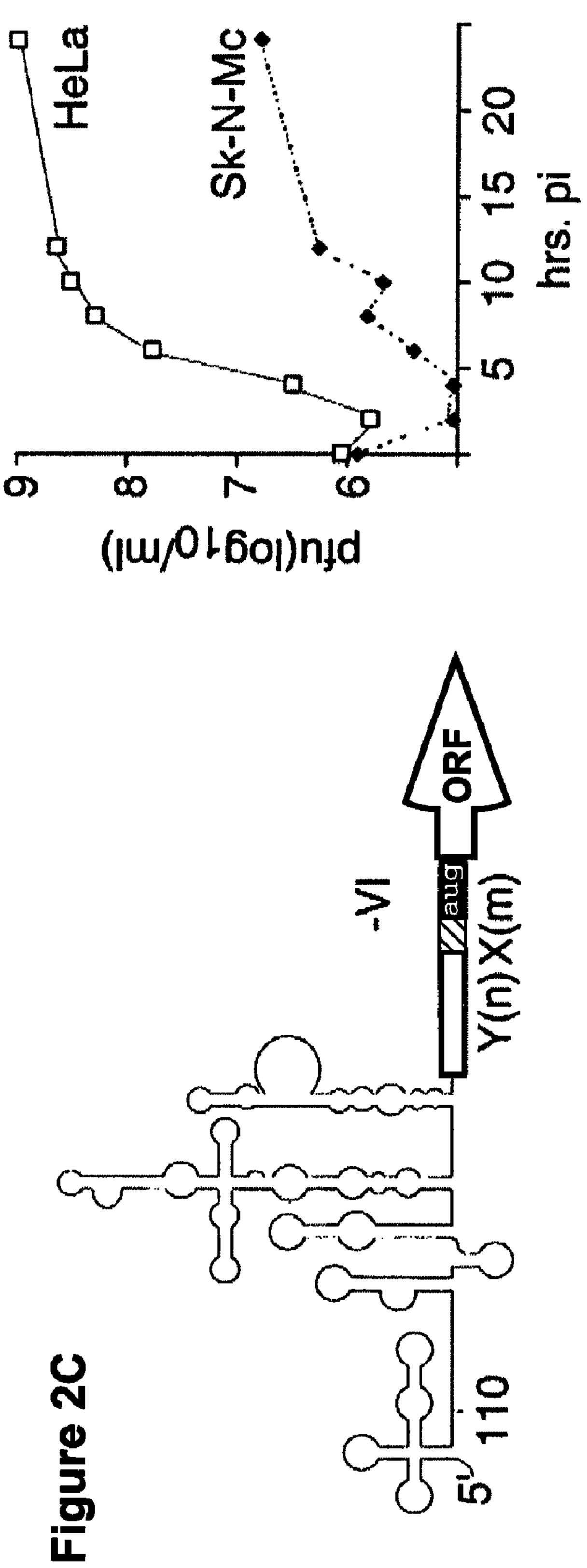

Rather than inserting foreign sequences into the intact poliovirus genome, cognate IRES sequences were replaced with heterologous ORFs. These expression constructs were generated by deletion of the HRV2 IRES stem-loop domain VI and upstream shift of the initiating AUG (FIG. 2). This was accomplished by taking advantage of conserved structure elements within picornaviral IRES elements: the polypyrimidine tract, or Y(n)X(m)AUG motif, is a standard feature of all picornaviral IRES elements (Wimmer et al, Ann. Rev. Genet. 27:353-436 (1993)). In polio- and rhinoviruses, the AUG contained within this motif is located at the base of stem-loop domain VI (FIG. 2A). It is not in Kozak context and never is used to initiate translation (Wimmer et al, Ann. Rev. Genet. 27:353-436 (1993)). Instead, an AUG triplet in Kozak context located 33 nt (HRV2) or 155 nt (poliovirus) downstream of Y(n)X(m)AUG serves as initiation codon (FIG. 2A). Sequences in between Y(n)X(m)AUG form stem-loop domain VI in both HRV2 and poliovirus, as well as a 132 spacer without predicted stable secondary structure in enteroviruses only (FIG. 2A).

It has been shown previously with poliovirus, that initiation of translation can be moved to Y(n)X(m)AUG by altering the context of its AUG triplet (Pestova et al, Virology 204:729-737 (1994)). Stem-loop domain VI of the HRV2 IRES was deleted and placed the Y(n)X(m)AUG was placed in Kozak context to produce a viable virus, PVS-δ6, which initiates translation from the Y(n)X(m)AUG motif (FIG. 2B). PVS-δ6 exhibited wild-type replication kinetics in HeLa cells and retained the neuronal replication defect of its progenitor PVS-RIPO (FIG. 2C; Gromeier et al, Proc. Natl. Acad. Sci. USA 93:2370-2375 (1996)).

Figures 1A, 1B, 1C, 1D:
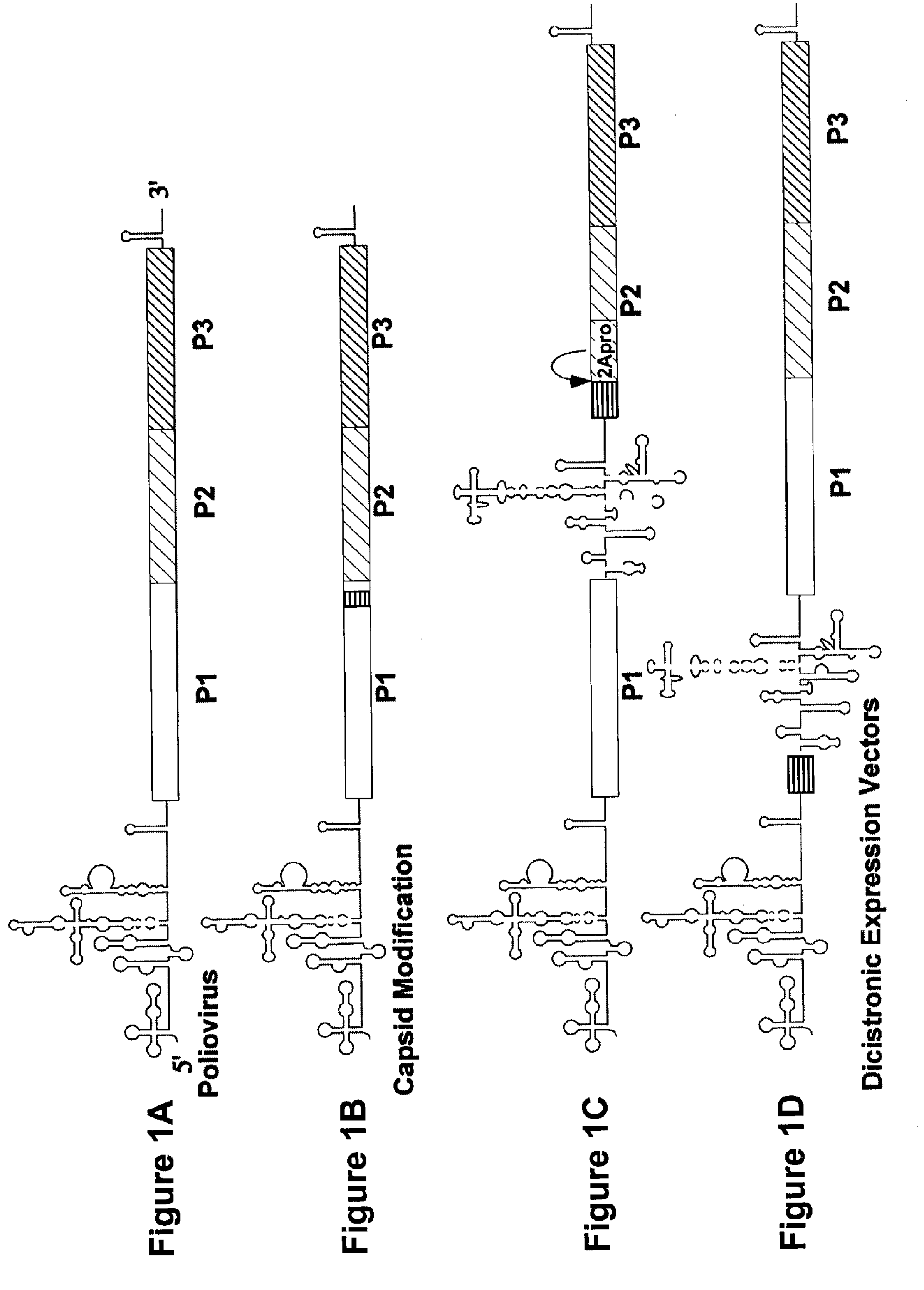
FIGS. 1A to 1G. Genetic structure of poliovirus-based expression vectors.
Figures 1E, 1F, 1G:
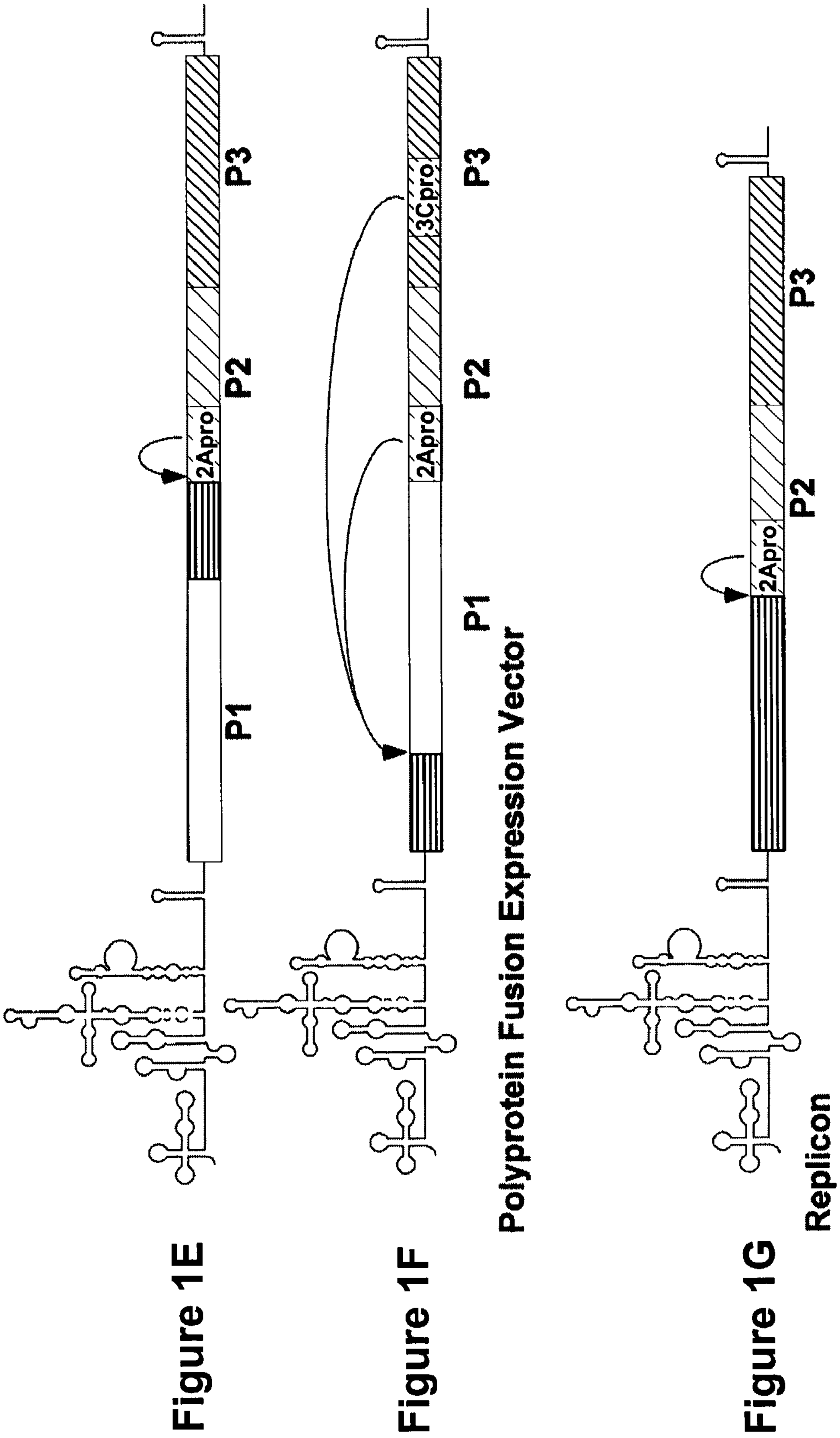

PVS-δVI was used as the backbone vector to generate poliovirus-based expression constructs. In designing the 3' junction of the expression cassette, a previously employed strategy was followed (Andino et al, Science 265:1448-1451 (1994), Mueller et al, J. Virol. 72:20-31 (1998)). This was accomplished by fusing sequences encoding foreign gene products with the coding region for the polioviral polyprotein (see FIG. 1F). Proteolytic processing of the fused transgene was achieved by inserting a cleavage recognition site for the virally encoded proteinase $2A^{pro}$ between the C-terminal end of the foreign insert and the N-terminus of polioviral P1 (compare FIG. 1F).

Figure 3A:
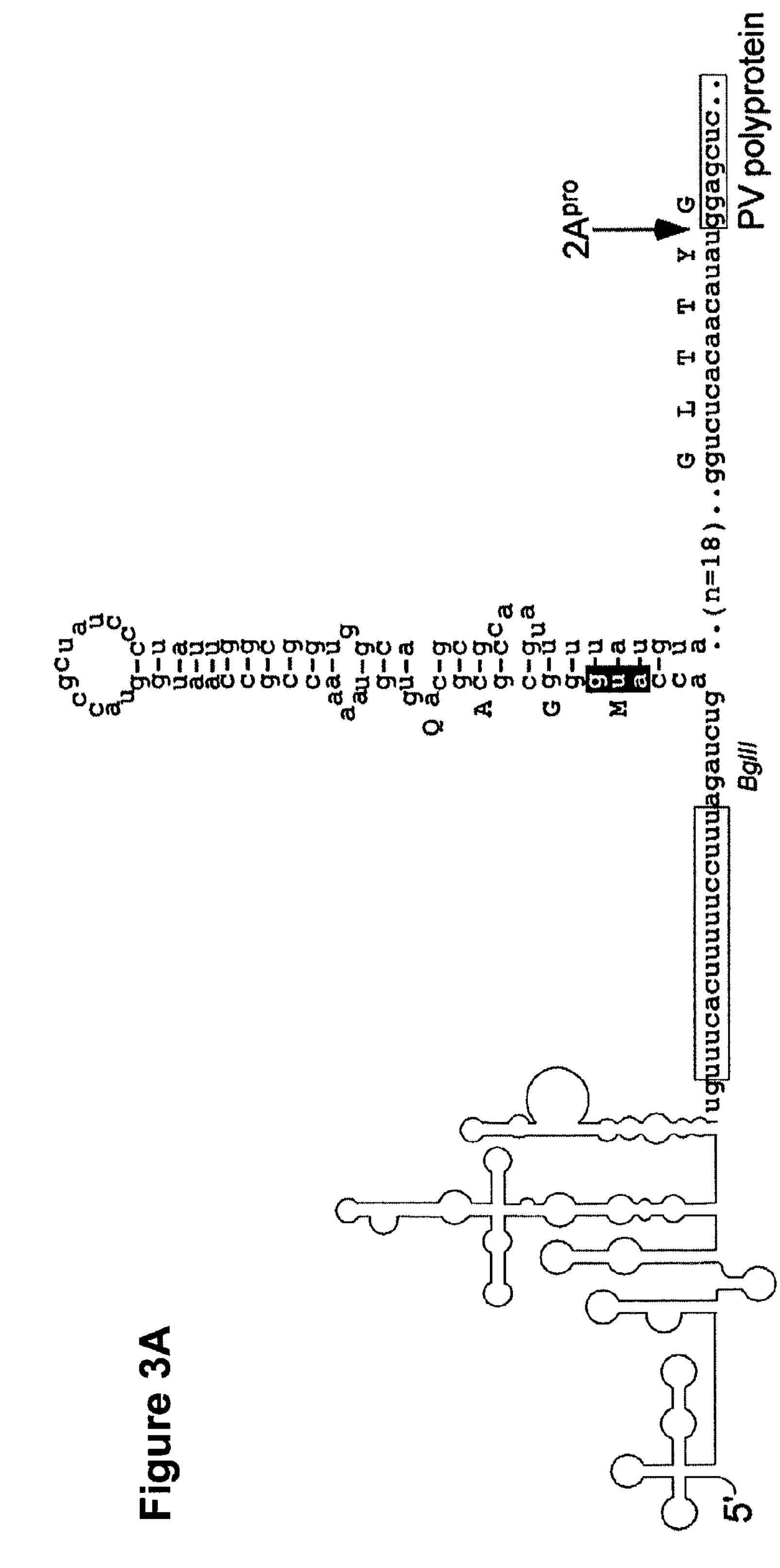
FIGS. 3A and 3B.

In a first set of experiments, an antigenic determinant of a bacterial adhesion molecule, FimH into PVS-δ6 was inserted (FIG. 3A). The chosen fragment of *E. coli* FimH was 75 nucleotides (nt) in length and was predicted to form a stable stem-loop structure in a position equal to HRV2 IRES stem-loop domain VI (compare with FIG. 1F).

Figure 3B:
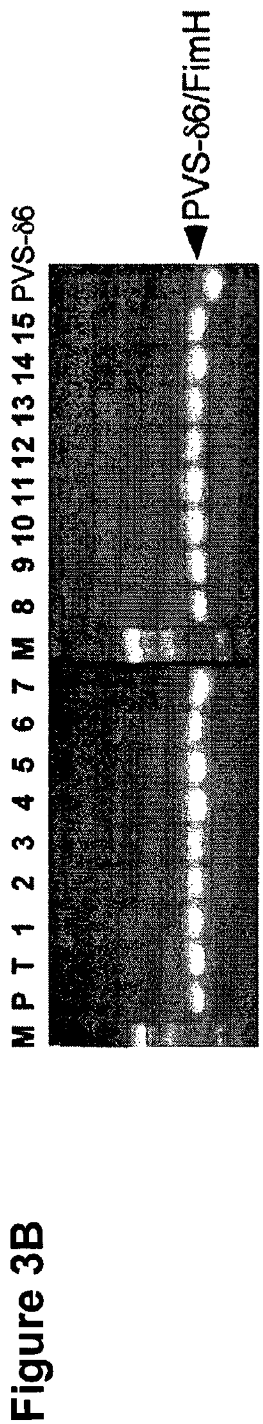

Viral RNA encoding the FimH expression construct was generated through in vitro transcription which was used to produce virus via transfection of HeLa cells. Thereupon, virus was subjected to 15 serial passages in HeLa cells. Total cellular RNA was isolated from infected cells after transfection and each subsequent passage. Total RNA served as template for reverse transcription-PCR amplification using primers annealing to the 5' cloverleaf (nt 76-92) of the viral genome and the 5' end of the poliovirus polyprotein ORF (nt 766-784; for relative position or primers, refer to FIG. 2A). PCR reactions yielded fragments representing IRES sequences including the FimH insert (FIG. 3B). After 15 passages in HeLa cells, the size of the PCR product indicated retention of inserted sequences throughout all passages (FIG. 3B). Sequencing of cDNA prepared from passage 15 through reverse transcription revealed the expression construct to remain intact as cloned.

Figure 4A:
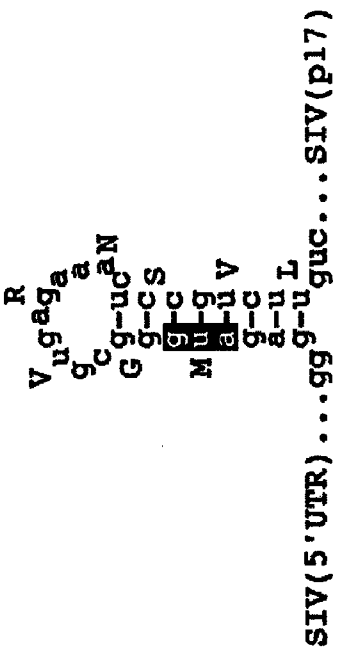
FIGS. 4A-4E.
Figure 4B:
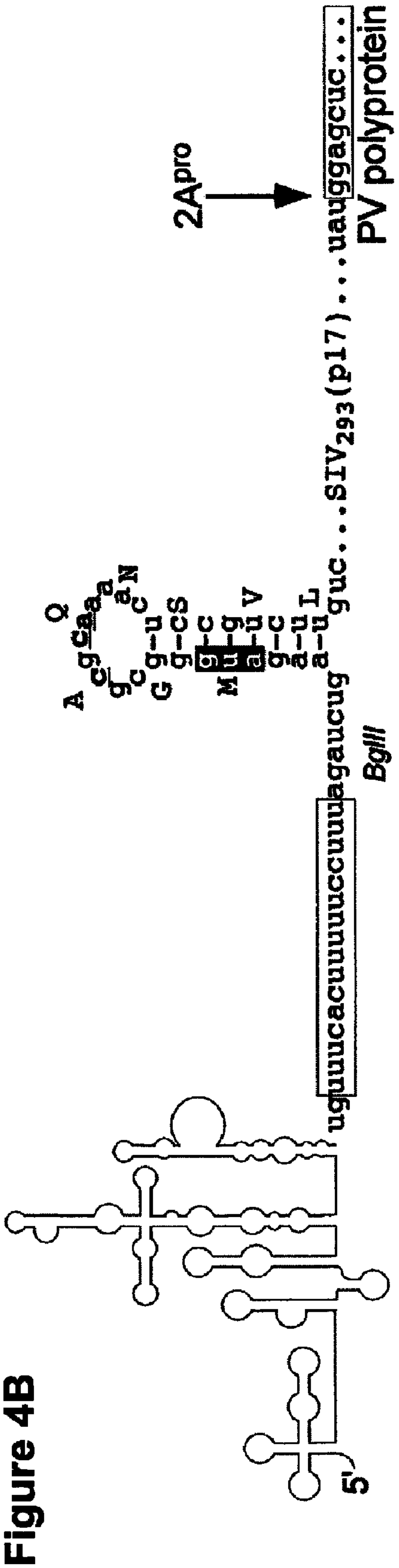

The observations indicated that, in contrast to full-length IRES expression vectors, coding sequences inserted into PVS-δ6 may be retained indefinitely. However, the relatively small size of the FimH insert may have benefited insert retention because it permitted creation of a structure mimicking the overall architecture of the HRV2 IRES. In order to assess retention of a much larger foreign sequence fragment, an expression vector was designed through insertion of the coding frame for simian immunodeficiency virus (SIV) p17 into PVS-δ6. Similar to the FimH construct, the aim was to maintain a stem-loop structure in the position previously occupied by IRES stem-loop domain VI. Advantage was taken of the presence of a predicted stable stem-loop structure of SIV-p17 RNA containing the initiating AUG (the "AUG loop"; FIG. 4A; Berkhout, Progr. Nucl. Acid Res. Mol. Biol. 54:1-34 (1996)). Manipulations necessary to insert a foreign open reading frame into PVS-δ6 were designed to maintain the general structure of the predicted AUG loop (FIG. 4B). As with the FimH construct (see FIG. 3A), to ensure proper processing of the viral fusion polypeptide, the authentic leader peptide of the wt poliovirus polyprotein (MGAQ; FIGS. 3A, 4B) was placed at the N-terminal junction of the expression cassette. These changes altered the N-terminus of SIV-p17 from MGVRNSVL (SEQ ID NO:45) to MGAQNSVL (SEQ ID NO:47). The introduction of these changes was designed not to alter the predicted stem-loop structure of the AUG loop (compare FIGS. 4A and B).

Figure 4C:
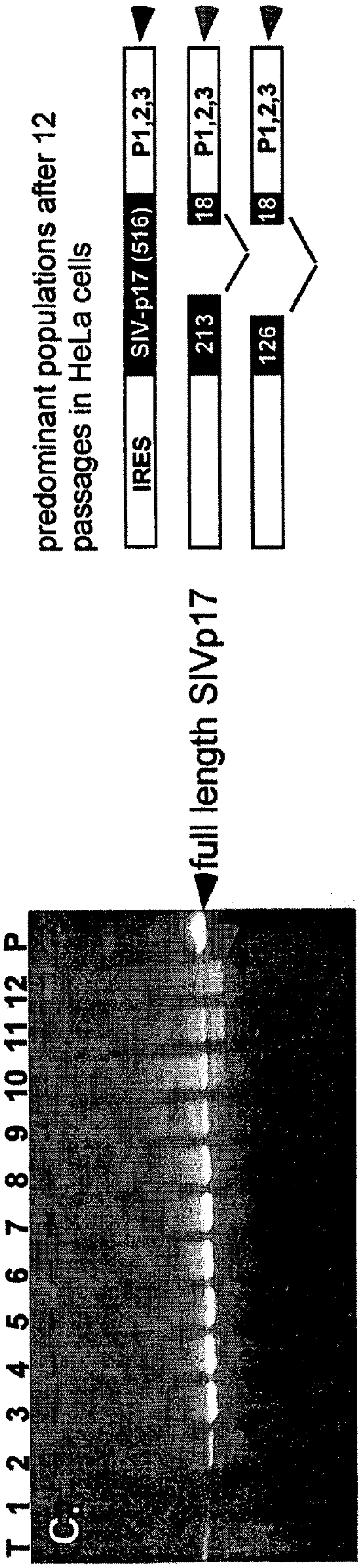

The SIV-p17 expression construct was subjected to serial passages and RT-PCR analyses as with the FimH construct (FIG. 4C). Retention of SIV sequences for 8 passages was observed, and gradual appearance of deletion variants thereafter. Even after 12 passages intact SIV-p17 sequences could still be recovered, indicating the presence of replicating original construct. Sequencing of three RT-PCR fragments observed after 12 passages revealed the full-length SIV-p17 sequence for the largest- and distinct truncated SIV-p17 sequences for the deletion fragments (FIG. 4C).

Figure 4D:
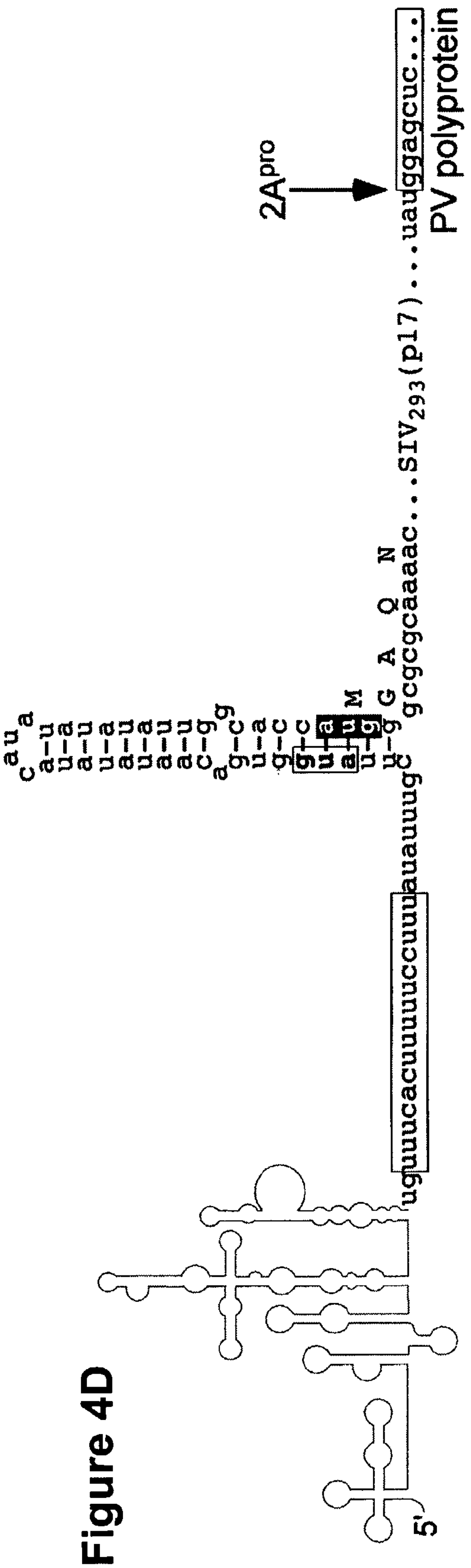
Figure 4E:
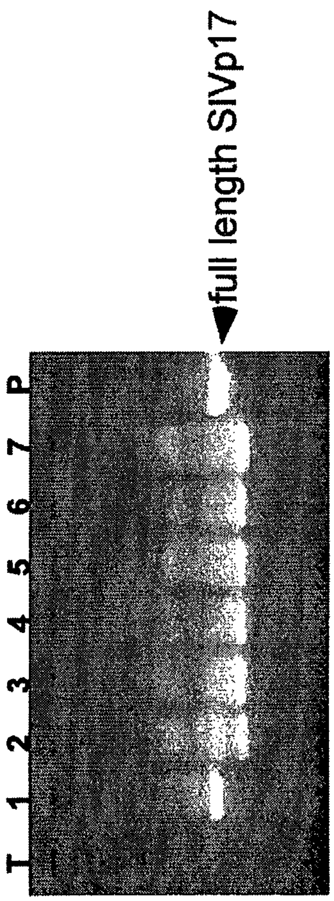

In order to compare relative genetic stability of the IRES deletion expression vector with previously reported designs (Andino et al, Science 265:1448-1451 (1994), Mueller et al, J. Virol. 72:20-31 (1998)), a SIV-p17 expression vector containing the intact HRV2 IRES (FIG. 4D) was reconstructed. The genetic structure of this construct was equivalent to the first reported polyprotein fusion vector (Andino et al, Science 265:1448-1451 (1994); compare FIGS. 1F, 4D). Serial passaging and RT-PCR sequencing studies were then conducted paralleling those performed before (FIG. 3B, 4C). In accordance with published analyses of the poliovirus polyprotein fusion expression vectors lacking genetic stability (see FIG. 1F), inserted genetic material was rapidly eliminated in its entirety (FIG. 4E). Within 2 passages after transfection, a prominent deletion variant had appeared. After 3 passages, RT-PCR analysis no longer produced fragments of the expected full length SIV-p17 size. Sequencing of the sole RT-PCR product obtained after 3 passages revealed wild-type PVS-RIPO sequence, indicating deletion of the entire heterologous insert.

Figure 5A:
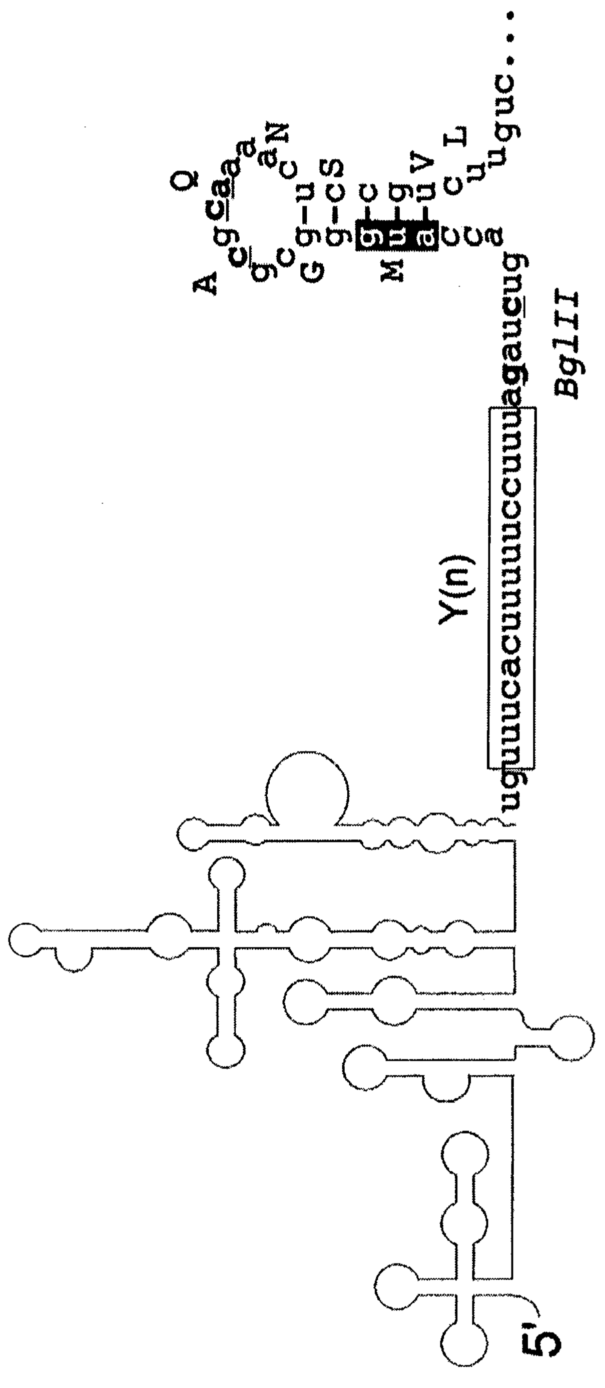
FIGS. 5A-5D.

Significantly enhanced insert retention was observed in expression vectors featuring foreign sequences mimicking IRES structures. This may indicate that overall IRES structure featuring a stable stem-loop domain VI (or its synthetic equivalent) is beneficial for virus replication. To further corroborate this hypothesis, PVS-RIPO/SIV-p17 expression vectors were constructed in which the stability of the AUG stem-loop domain was slightly compromised (FIG. 5). This was accomplished by changing the context of the initiating Y(n)X(m)AUG from aagAUGg (FIG. 4B) to accAUGg (FIG. 5A). The latter would disrupt base-pairing of the lower stem of the SIV AUG domain and, thus, predictably weaken stem-loop integrity.

Figure 5B:
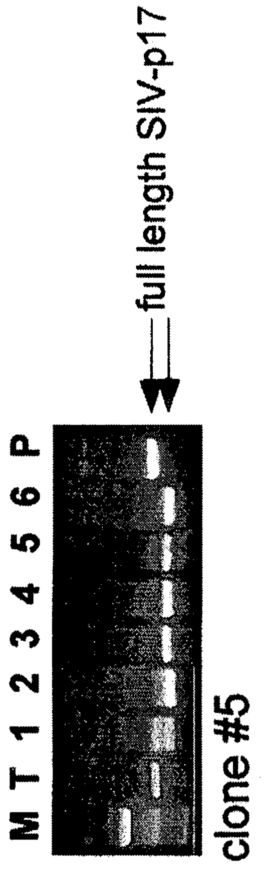

Virus generated from cDNA clones featuring Y(n)X(m) accAUGg ($SIV_{acc}AUG$) was subjected to the identical passaging/RT-PCR sequencing regimen employed in prior analyses. Surprisingly, $SIV_{acc}AUG$ displayed fundamentally different genetic stability compared to $SIV_{aag}AUG$ (FIG. 5B). Transfections of three separate clones yielded virus progeny that had equally poor genetic stability profiles as the full-length IRES expression vector (compare FIGS. 4E and 5B).

Figure 5C:
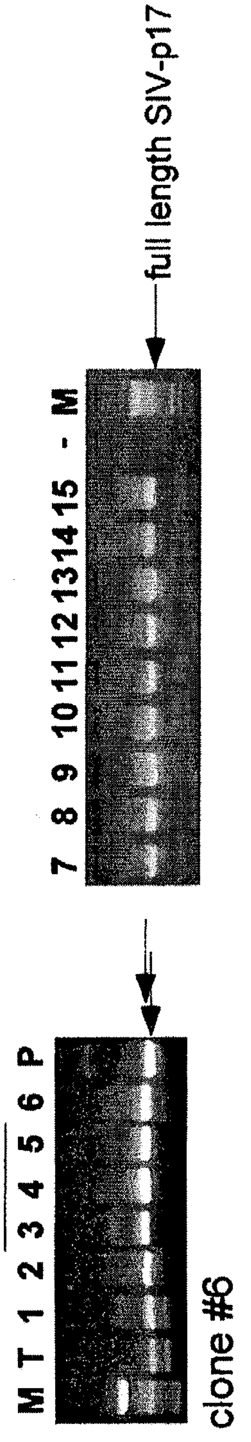
Figure 5D:
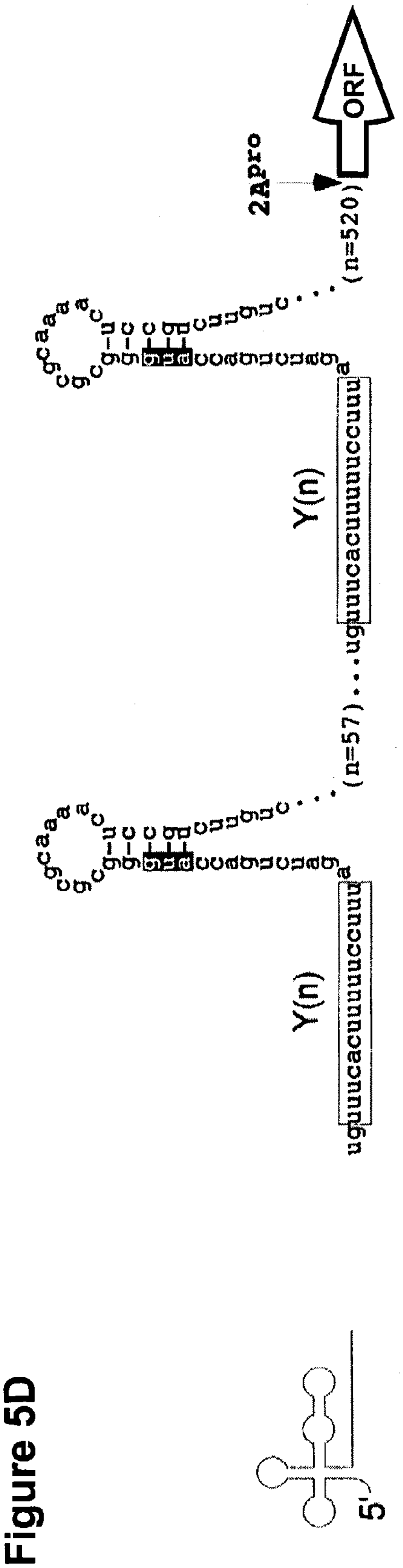

However, passaging transfected $SIV_{acc}AUG$ yielded a most interesting adaptation mutant, where insert sequences were not deleted but enlarged instead (FIG. 5C). This observation was completely unexpected, since reversion to a faster growing phenotype invariably involved deletion events shrinking or eliminating inserted heterologous sequences. Sequencing of the enlarged insert from revertant $SIV_{acc}AUG$ revealed a most intriguing genetic modification. A complete duplication of sequences spanning Y(n)X(m)AUG, the AUG stem-loop domain, and 63 nt of the 3' SIV-p17 insert (FIG. 5D) was detected. The duplication was in frame, producing two tandem AUGs in Kozak context, the second of which leading the intact SIV-p17 insert sequence (FIG. 5D).

The fact that replicating $SIV_{acc}AUG$ virus reacted by enlarging insert sequences rather than abandoning them suggested the lengthened insert to contribute to enhanced virus replicative ability. The duplication step occurred in the $2^{nd}$ passage, at the same time when deletion events in genetically unstable expression constructs took place (see FIG. 5B). If the enhanced insert indeed conferred increased fitness to the revertant virus, the altered sequence would be expected to be genetically stable. To test this, serial passaging experiments were performed for up to 15 passages (FIG. 5C). Sequencing of the revertant passaged construct indicated, indeed, the intact SIV-p17 insert as well as the duplicated Y(n)X(m)AUG motif/AUG stem-loop domain to be retained after 15 passages (FIG. 5D).

EXAMPLE II

Construction of IRES deletion recombinants and insertion of foreign ORFs. PVS-RIPO, a highly attenuated chimeric virus containing the human rhinovirus type 2 (HRV2) IRES in a poliovirus type 1 (Sabin) [PV1(S)] background (Gromeier et al, Proc. Natl. Acad. Sci. USA 93:2370-2375 (1996)), was used as the backbone vector to generate poliovirus-based expression constructs (FIG. 7). This recombinant virus chimera was chosen because evaluation of neurovirulence of PV1(RIPO), containing the HRV2 IRES within the genome of poliovirus type 1 (Mahoney), in non-human primates revealed levels of attenuation equal to PV1(S) (Gromeier et al, J. Virol. 73:958-964 (1998)). The construction of fusion polyprotein expression vectors to increase long-term retention and expression of foreign sequences was effected by replacing parts of the HRV2 IRES with heterologous ORFs of varying size. Picornavirus IRESes feature highly conserved structural elements predicted to form stable stem-loop domains (SLD; Le et al, J. Mol. Biol. 216:729-741 (1990), Pilipenko et al, Virology 168:201-209 (1989), Siu et al, J. Mol. Biol. 207:379-392 (1989)). These predicted hairpin structures are separated by linear sequence motifs that may display a surprising level of sequence conservation amongst picornaviruses.

Figure 7A:
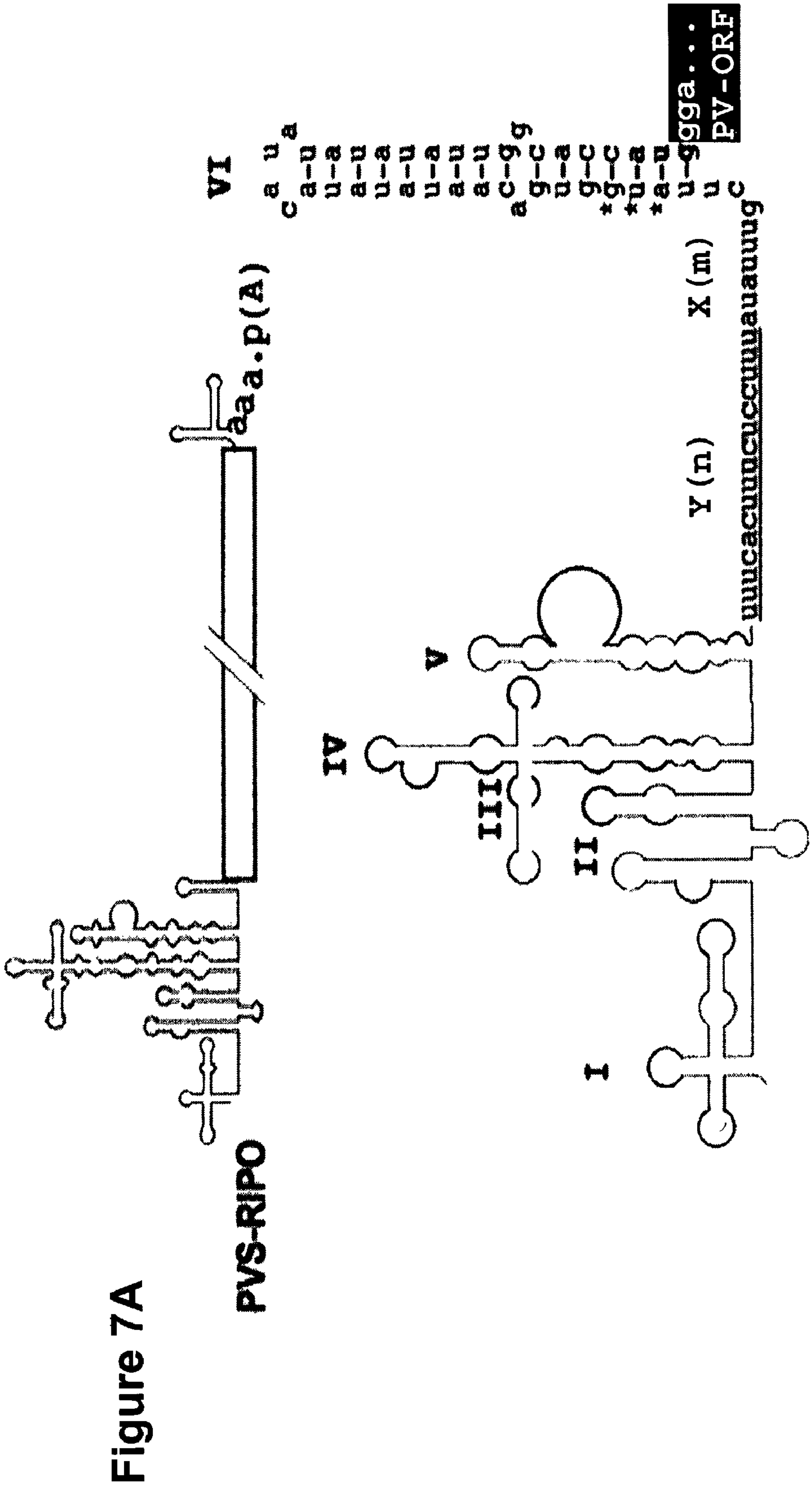
FIGS. 7A-7C.

The most thoroughly studied sequence motif within picornavirus IRES elements is a conserved linear polypyrimidine stretch located in between SLDs V and VI (FIG. 7; Iizuka et al, J. Virol. 63:5354-5363 (1989), Meerovitch et al, J. Virol. 65:5895-5901 (1991), Pestova et al, J. Virol. 65:6194-6204 (1991), Pilipenko et al, Cell 68:119-131 (1992), Wimmer et al, Annu. Rev. Genet. 27:353-436 (1993)). The Y(n)X(m) AUG motif contains a cryptic AUG codon that is never used to initiate translation (Pestova et al, J. Virol. 65:6194-6204 (1991), Wimmer et al, Annu. Rev. Genet. 27:353-436 (1993)). Instead, an AUG triplet located 33 nt (HRV2) or 155 nt (poliovirus) downstream of Y(n)X(m)AUG serves as initiation codon for the viral polyprotein synthesis (FIG. 7A).

Figure 7B:
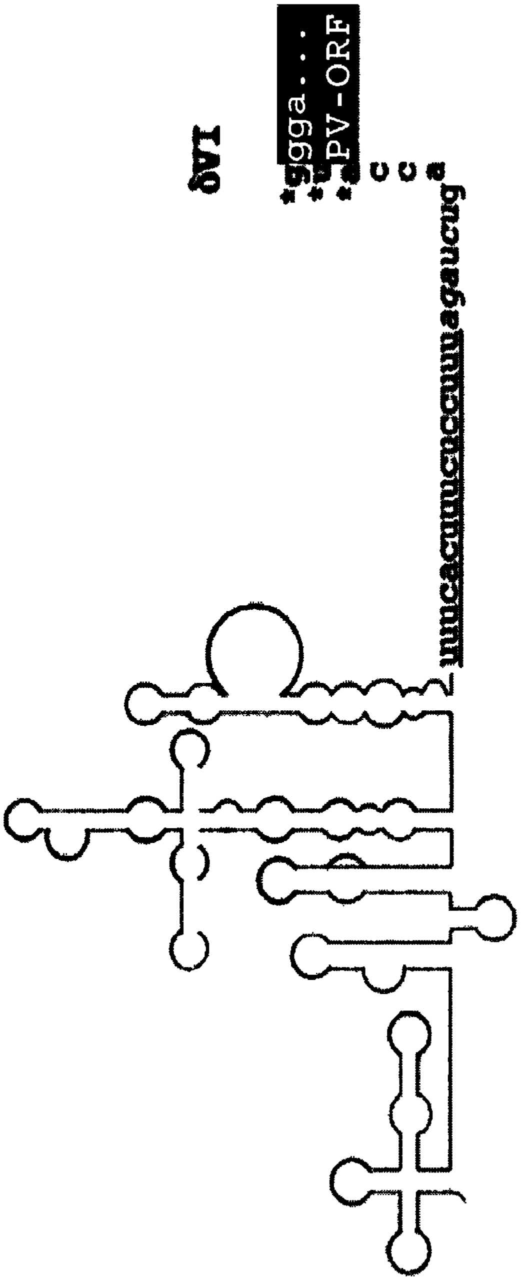
Figure 7C:
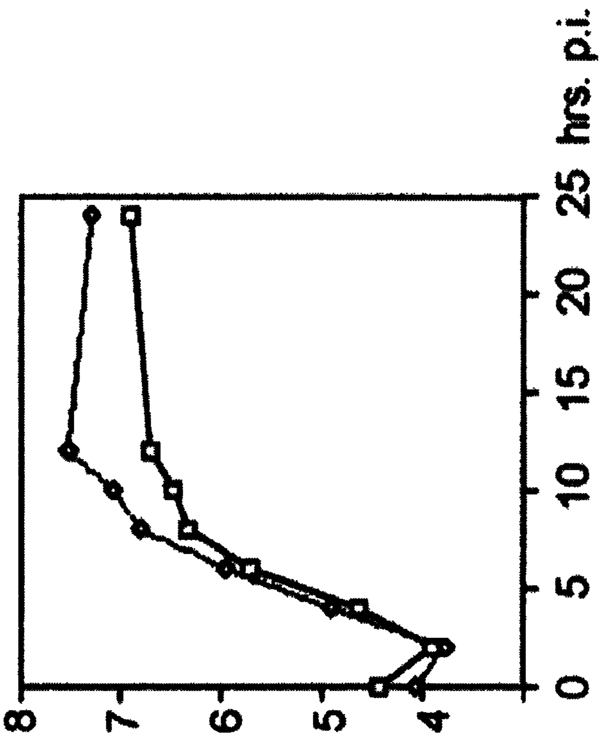
Figures 8A, 8B, 8C, 8D:
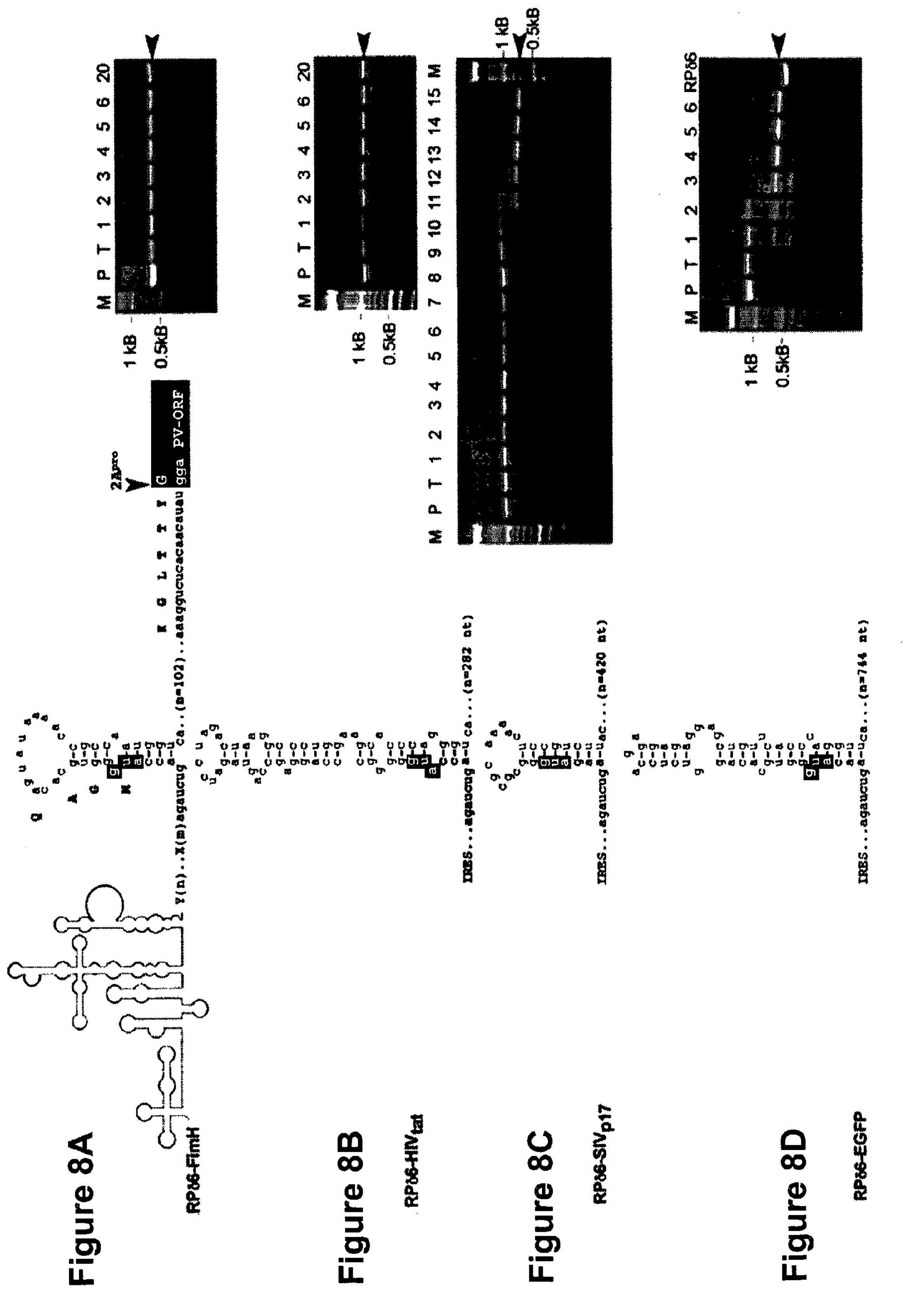
FIGS. 8A-8D. RPδ6 expression vectors containing deletions of SLD VI replaced by foreign ORFs. Heterologous sequences of FimH (FIG. 8A (SEQ ID NO:8 and SEQ ID NO: 10)) (SEQ ID NO:9), HIV-tat (FIG. 8B (SEQ ID NO:11)), and EGFP (FIG. 8D (SEQ ID NO:13)) were manipulated to recapitulate the predicted secondary structure of SLD VI and inserted into RPδ6. SIV-p17 (FIG. 8C (SEQ ID NO:12)) is predicted to form the 'AUG' loop naturally (Berkhout, Prog. Nucleic Acid Res. Mol. Biol. 54:1-34 (1996)). RT-PCR analyses of serial passages of individual expression constructs are shown in the right panel. Total cytoplasmic RNA was prepared from infected cultures corresponding to each passage and used as a template for RT and subsequent PCR using primers annealing to the 5' cloverleaf structure and the coding region for the viral polyprotein. PCR product corresponds to a region of the viral genome spanning the entire IRES, foreign insert, artificial proteolytic cleavage site, and N-terminal viral polyprotein. Arrowheads demarcate intact insert [after 20 passages; FimH (FIG. 8A) and HIV-tat (FIG. 8B)] or deletion variants [SIV-p17 (FIG. 8C) and EGFP (FIG. 8D)]. Foreign sequences are shown in blue, the artificial $2A^{pro}$ cleavage site separating foreign sequences from the viral ORF is indicated in red and the initiating AUG triplet is represented by a black box.

It has been previously shown for poliovirus (Pestova et al, Virology 204:729-737 (1994)) that translation initiation can be moved to Y(n)X(m)AUG by altering the context of its AUG triplet. Stem-loop domain VI of the HRV2 IRES in PVS-RIPO was deleted and placed the Y(n)X(m)AUG in Kozak context ( . . . cuuaug . . . to . . . accaug . . . ; FIG. 7B). This manipulation yielded a viable virus, RPδ6, which exhibited growth kinetics in HeLa cells similar to the parental PVS-RIPO (FIG. 7C). RPδ6 was used as the backbone vector to generate poliovirus-based expression constructs containing heterologous ORFs partially replacing IRES sequence (FIGS. 8A-D). Foreign genes were inserted immediately downstream of the Y(n)X(m)AUG motif, which supplied the initiation codon for the fusion polyprotein (FIG. 8A). The sequence encoding the N-terminal four amino acids of the polioviral polyprotein (MGAQ . . . ) was placed at the 5' junction of the expression cassette to ensure proper processing of the fusion polyprotein (FIG. 8A). The 3' junction of the foreign insert and the polioviral ORF contained the sequence encoding an artificial cleavage site for the viral proteinase 2A ($2A^{pro}$; . . . KGLTTY'G . . . (SEQ ID NO:9); FIG. 8A) (Andino et al, Science 265:1448-1451 (1994), Crotty et al, J. Virol. 73:9485-9495 (1999)). Thus, post-translational proteolytic cleavage of the fusion polyprotein was predicted to release foreign and viral polypeptides without impediment to virus viability.

Insert size and genetic stability of polio expression vectors with truncated IRESes. A series of expression constructs were generated. First, the influence of insert size on genetic stability was tested (FIG. 8A-8D). For this purpose, RPδ6 expression vectors containing inserts encompassing the ORFs of a bacterial antigen (FimH; 102 nt), human immunodeficiency virus tat protein ($HIV_{tat}$; 282 nt), simian immunodeficiency virus matrix protein ($SIV_{p17}$; 420 nt), and the enhanced green fluorescent protein (EGFP; 744 nt), respectively, were generated (FIG. 8A-8D). The insert length indicated comprises sequences coding for the leader peptide and the artificial proteolytic cleavage site.

The 5'-terminal sequences of the foreign inserts in RPδ6-FimH, RPδ6-$HIV_{tat}$, and RPδ6-EGFP were modified by silent mutagenesis to form a predicted stable stem-loop structure in a position equal to HRV2 IRES domain VI (see sequence detail in FIGS. 8A, 8B, 8D). RPδ6-$SIV_{p17}$, by virtue of the presence of the 'AUG' loop in the SIV 5' leader (Berkhout, Prog. Nucleic Acid Res. Mol. Biol. 54:1-34 (1996)), naturally formed a stable stem-loop structure reminiscent of the HRV2 IRES domain VI (FIG. 8C).

All four expression constructs produced viable viruses, but RT/PCR analysis of viral genomic RNA in serial passages in HeLa cells revealed that insert retention varied dramatically (FIG. 8A-8D). Whereas RPδ6-FimH (102 nt insert) and RPδ6-$HIV_{tat}$ (282 nt insert) retained the full-length insert throughout at least 20 subsequent passages (FIGS. 8A, 8B), expression constructs containing larger foreign ORFs were less stable. Serial passage of RPδ6-$SIV_{p17}$ (420 nt insert) revealed the emergence of deletion variants 9 passages after transfection, and foreign sequences within RPδ6-EGFP (744 nt insert) were deleted already during the first passage (FIG. 8D).

These observations indicate that poliovirus expression vectors can be designed to permanently retain foreign ORFs using integration of heterologous inserts into 5' regulatory elements. Furthermore, the experiments indicated inserts >300 nt in length to exceed the size restraints imposed by the location of the insert and to trigger deletion events.

Figures 9A, 9B:
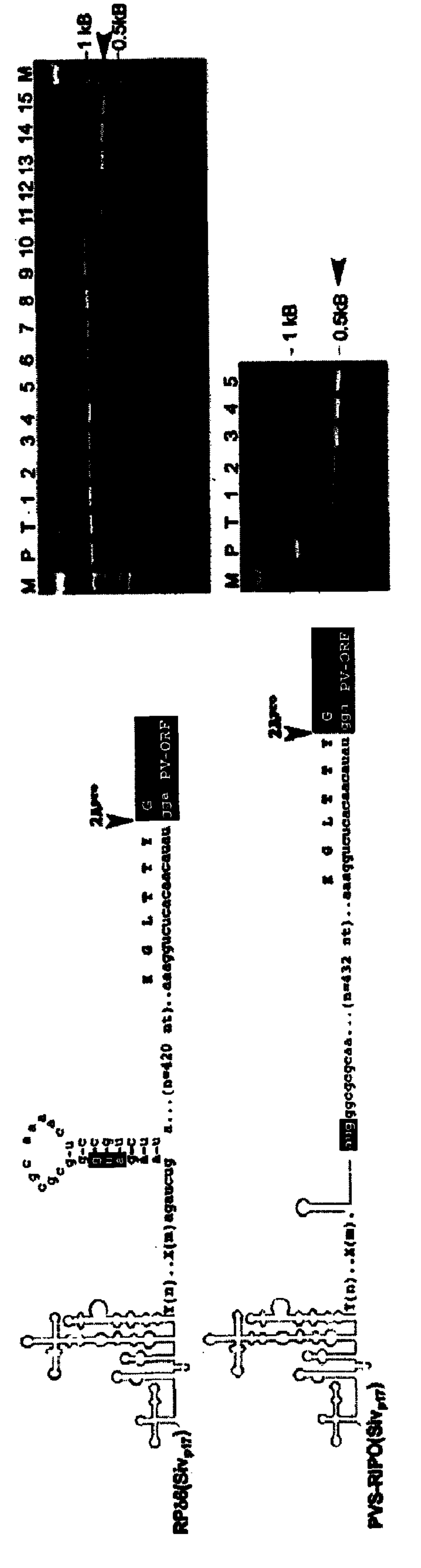
FIGS. 9A and 9B.

Despite the diminished genetic stability of RPδ6-$SIV_{p17}$ and RPδ6-EGFP, the approach produced prototype expression vectors that exhibited far superior retention of foreign ORFs than previously reported strategies to generate polyprotein fusion vectors (Andino et al, Science 265:1448-1451 (1994), Crotty et al, J. Virol. 73:9485-9495 (1999)). These vectors, independently of insert size, reportedly are characterized by a high degree of genetic instability (Mueller and Wimmer, J. Virol. 72:20-31 (1998)). This difference was evident when RPδ6-$SIV_{p17}$ was compared with 'conventional' polyprotein fusion vectors constructed according to the blueprint of Andino et al. (1994) (Dufresne et al, J. Virol. 76:8966-8972 (2002)); FIG. 9). Whereas RPδ6-$SIV_{p17}$ retained the full-length $SIV_{p17}$ ORF for at least 9 passages (FIG. 9A), the 'conventional' PVS-RIPO-$SIV_{p17}$ (containing the entire IRES element) eliminated the foreign insert already after the $1^{st}$ passage (FIG. 9B). Interestingly, deletion of foreign sequences in RPδ6-$SIV_{p17}$ never removed the entire insert, but involved long-term retention of ~40% of heterologous sequences (Dufresne et al, J. Virol. 76:8966-8972 (2002)); FIG. 9B; compare the size of the endpoint deletion product in A and B). In contrast, passaging of PVS-RIPO-$SIV_{p17}$ invariably led to the elimination of >98% of the heterologous insert (FIG. 9B).

Structural features dictating insert retention. The observations indicated that viruses where conserved IRES features (e.g., SDL VI) were replaced with foreign inserts displayed superior insert retention over variants where insert sequences were merely added to the viral genome (Andino et al, Science 265:1448-1451 (1994), Crotty et al, J. Virol. 73:9485-9495 (1999)). These findings corroborated the basic assumption that if heterologous ORFs could be inserted into viral genomes to confer a replicative advantage (by replacing deleted structural elements), permanently stable expression vectors could be derived.

Figures 10A, 10B, 10C:
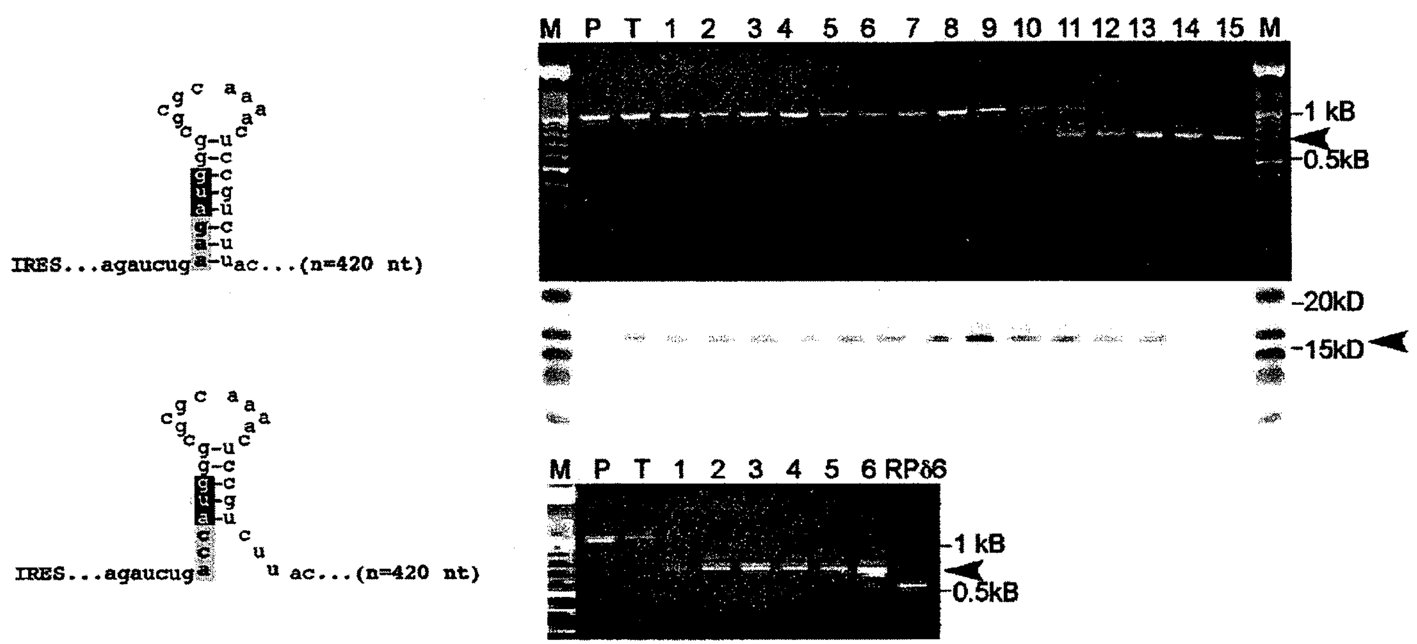
FIGS. 10A-10C. Genetic structure of RPδ6-$SIV_{p17}$-aag (FIG. 10A (SEQ ID NO:12)) and RPδ6-$SIV_{p17}$acc (FIG. 10C). Characterization of the constructs was carried out as described in FIG. 8. The results of serial passaging and RT/PCR analysis are shown in the right panel.

To solidify this hypothesis, the influence of predicted secondary structure on insert retention of RPδ6 expression vectors was evaluated. Since part of the strategy is based on the functional replacement of IRES SLD VI, the secondary structure assumed by the foreign insert replacing SLD VI is likely to influence IRES function and, therefore, insert retention. RPδ6-$SIV_{p17}$ was chosen to alter the predicted stability of the artificial stem loop domain VI formed by heterologous sequences (FIG. 10). The initiating AUG codon of $SIV_{p17}$ is located within the 'AUG' loop of the SIV leader in a position similar to that of the cryptic AUG within the Y(n)X(m)AUG motif of picornaviruses (FIG. 10A, compare FIG. 8C). Two expression vectors (RPδ6-$SIV_{p17}$-acc and RPδ6-$SIV_{p17}$-aag) were constructed differing only in the sequence of 2 nucleotides immediately upstream the initiating AUG codon ( . . . accaugg . . . vs . . . aagaugg . . . ) (FIG. 10). Both sequences placed the initiating codon in Kozak context and maintained the predicted overall structure of the 'AUG' loop. However, in the RPδ6-$SIV_{p17}$-acc construct, the ACC triplet disrupted base pairing that was predicted to increase the stability of the SLD formed by $SIV_{p17}$ sequences (FIG. 10C).

RT-PCR analysis revealed a significantly decreased retention of the foreign ORF in RPδ6-$SIV_{p17}$-acc, due to the minor alteration resulting in weakening of the recombinant stem-loop domain VI (FIG. 10C). Similar to expression constructs containing the full-length IRES (compare with FIG. 9B), RPδ6-$SIV_{p17}$-acc displayed deletions of $SIV_{p17}$ sequences already after the $1^{st}$ passage after transfection (FIG. 10C). In contrast, RPδ6-$SIV_{p17}$-aag, merely differing by a slightly more stable stem-loop structure, retained the intact $SIV_{p17}$ insert for at least 9 subsequent passages (FIG. 10A). Western blot analysis of cell lysates from consecutive passages of RPδ6-$SIV_{p17}$-aag was consistent with RT-PCR data revealing $SIV_{p17}$ expression in tandem with insert retention (FIG. 10B). $SIV_{p17}$ expression was detected until the $13^{th}$ passage, when full-length insert could no longer be amplified by RT-PCR analysis (compare FIG. 10A, 10B). It is speculated that RT-PCR analysis favors amplification of shorter deletion variants, thereby suppressing signal due to remaining intact RPδ6-$SIV_{p17}$-aag at later passages.

Artificial stable SLDs favor retention of IRES inserts. The observations suggested that the secondary structure of foreign sequences inserted to replace IRES SLD VI might influence the genetic stability of RPδ6 expression vectors. Constructs with foreign inserts predicted to form stable SLDs mimicking the architecture of IRES domain VI could have advantages over non-structured inserts with regard to retention of heterologous sequences. To corroborate this hypothesis, the predicted stability of SLDs formed by poliovirus expression vectors with permanently retained inserts was modified. For this purpose, RPδ6-$HIV_{tat}$, a vector that retains a 282 bp foreign insert for at least 20 passages, was chosen (FIG. 8B). Three expression vectors, RPδ6-$HIV_{tat}$(1)-(3) were constructed with inserts differing in the predicted stability of the artificial SLD VI formed by $HIV_{tat}$ coding sequences (FIG. 11).

Figures 11A, 11B, 11C:
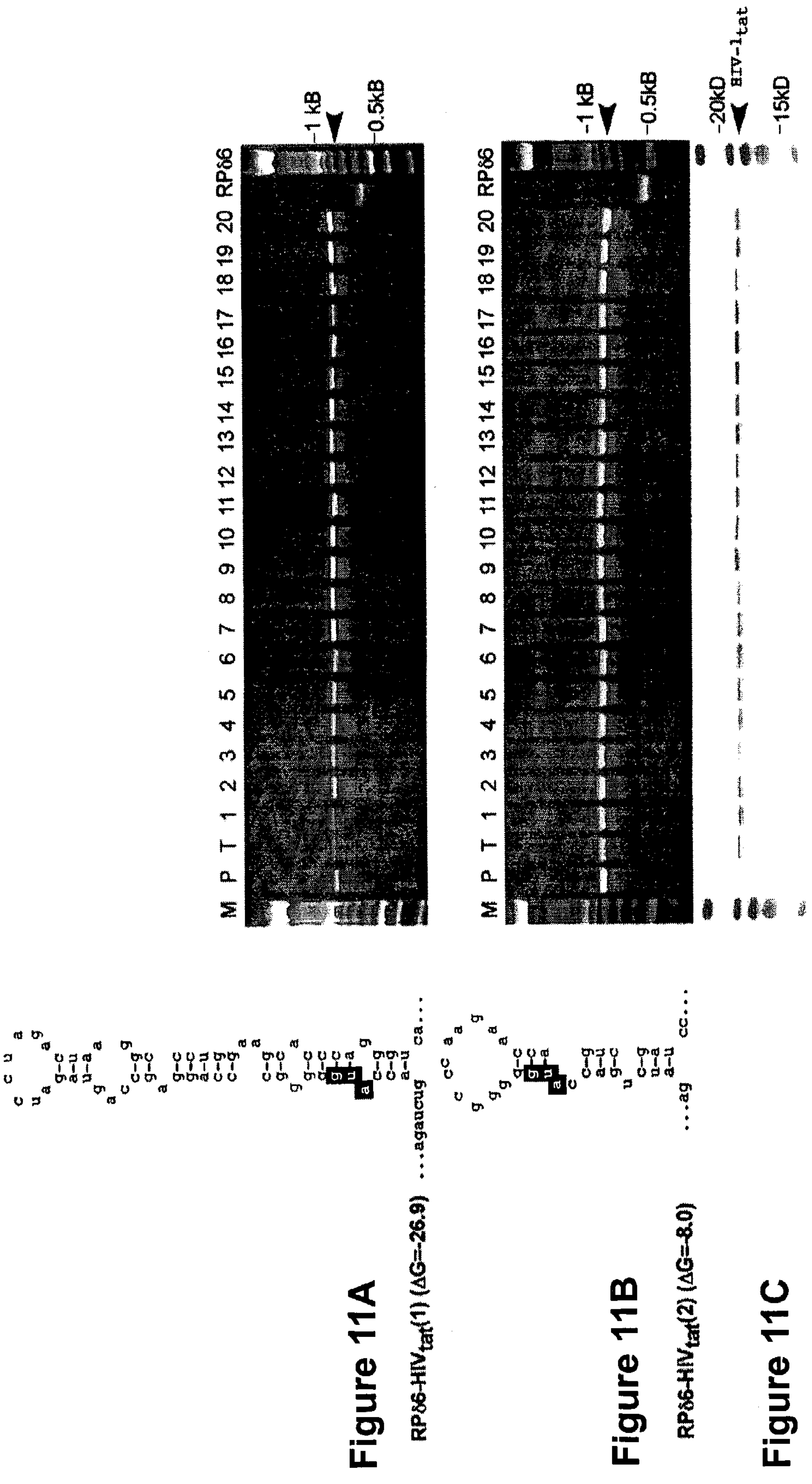
FIGS. 11A-11F. Genetic structure and insert retention of RPδ6-$HIV_{tat}$ variants with divergent predicted stability of the artificial SLDVI.
Figures 11D, 11E, 11F:
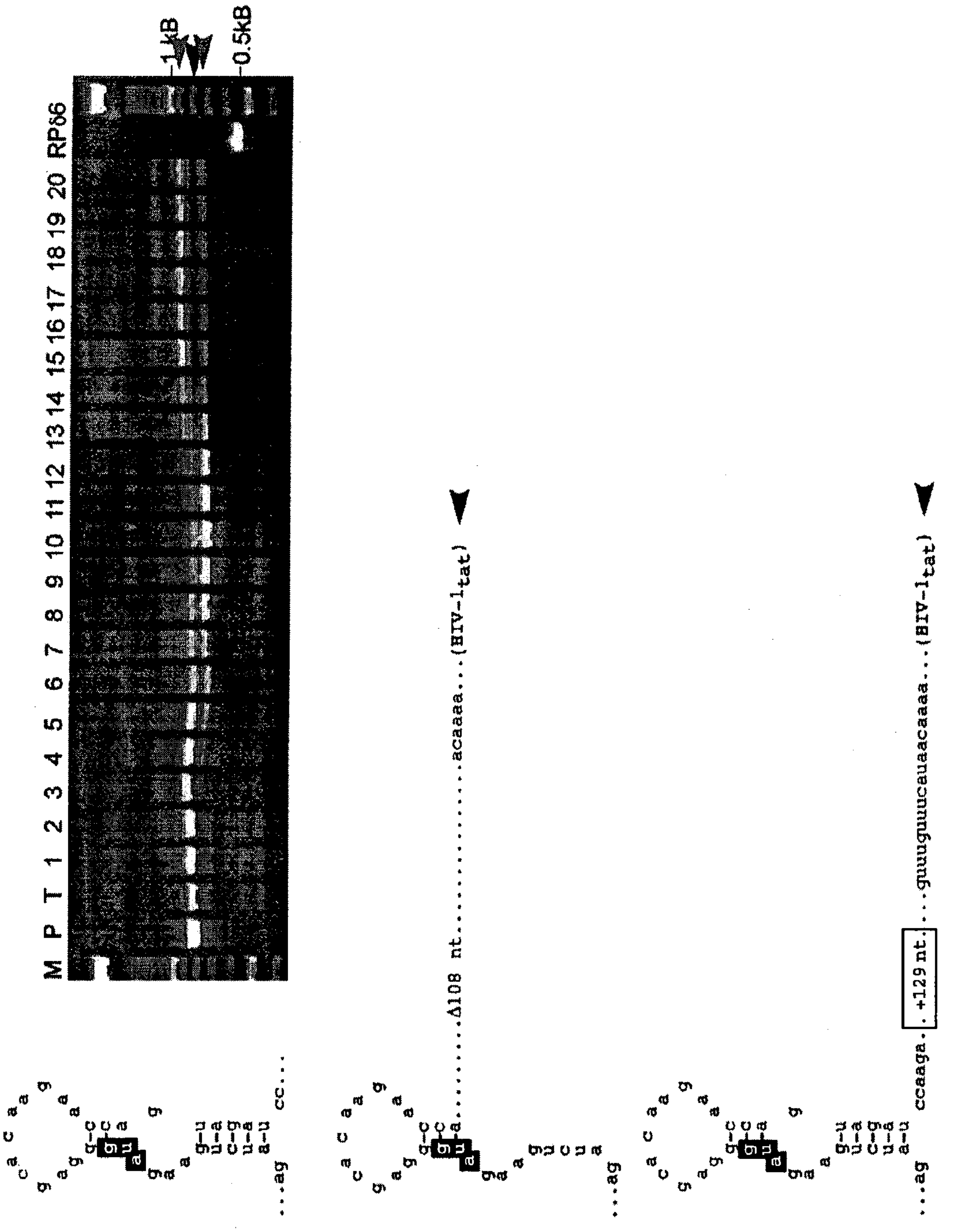

The RPδ6-$HIV_{tat}$(1) and RPδ6-$HIV_{tat}$(2) constructs with relatively strong and moderate secondary structures forming stem-loop domain VI (ΔG=−26.9 kcal/mole and −8.0 kcal/mole, respectively, FIG. 11A, 11B), were stable for at least 20 serial passages (FIG. 11A, 11B). In contrast, RPδ6-$HIV_{tat}$(3) (ΔG=−6.5 kcal/mole) acquired deletions in the $HIV_{tat}$ insert after the $3^{rd}$ passage (FIG. 11D). Notwithstanding the appearance of deletion variants, full-length insert could still be detected after 20 passages (FIG. 11D). Surprisingly, upon appearance of deletion variants, a variant containing an enlarged insert was also detected, emerging after the $11^{th}$ passage of RPδ6-$HIV_{tat}$(3) in HeLa cells (FIG. 11D). RT-PCR data indicated that the enlarged variant rapidly became predominant in the viral population, evident from the intensities of the amplification products (see FIG. 11D), suggesting a beneficial effect of insert enlargement leading to increased fitness over RPδ6-$HIV_{tat}$(3) and its deletion variants.

Sequencing of the deletion variant emerging upon serial passages of RPδ6-$HIV_{tat}$(3) revealed a 108 nt internal deletion within the ORF for $HIV_{tat}$ (FIG. 11E). This deletion retained only a remnant stem-loop structure VI (FIG. 11). Interestingly, sequencing of the enlarged RPδ6-$HIV_{tat}$(3) variant revealed replacement of an internal fragment of 84 nt of the $HIV_{tat}$ ORF with a 129 nt duplication of viral coding sequences for the capsid protein VP1 (nt 2986-3115) (FIG. 11F). This finding directly supported the hypothesis of the beneficial effects on virus replication of sequences inserted to replace IRES sequences in between Y(n)X(m)AUG and the true initiation codon (nt#743). The fact that replicating virus acquired additional sequences in that region during serial passages (resulting in superior growth properties; FIG. 11D) demonstrated the virus' preference for a certain structural arrangement including spacer sequences separating Y(n)X(m)AUG from the ORF of the viral polyprotein.

Figure 12B:
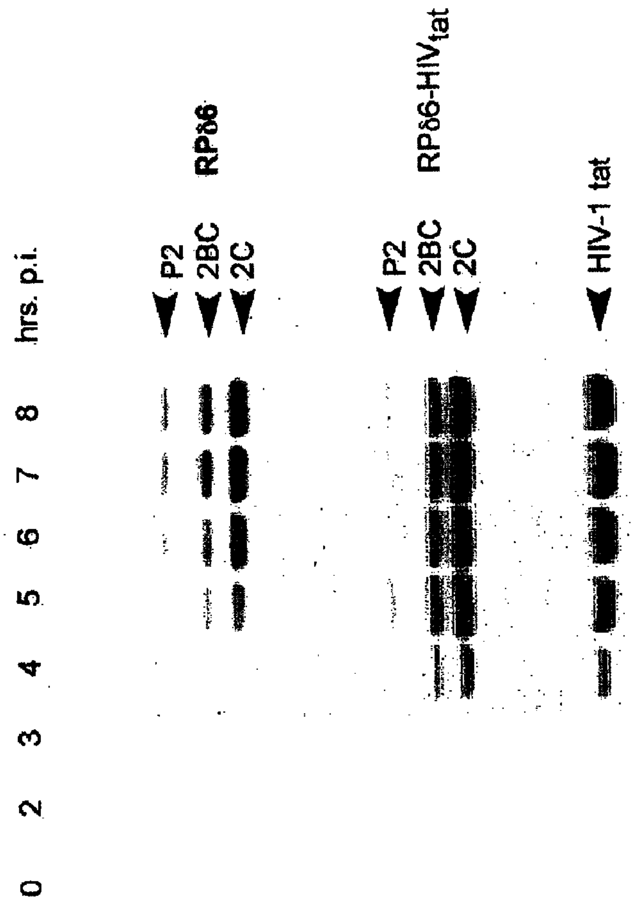
FIGS. 12A and 12B. Replication kinetics (FIG. 12A) and viral gene expression (FIG. 12B) of RPδ6-$HIV_{tat}$ (2) (open squares) and its parent RPδ6 (open diamonds). Expression of RPδ6-$HIV_{tat}$ (2) viral gene products and foreign insert ($HIV_{tat}$) (blue labeling) occurred in parallel and were accelerated when compared to RPδ6.
Figure 12A:
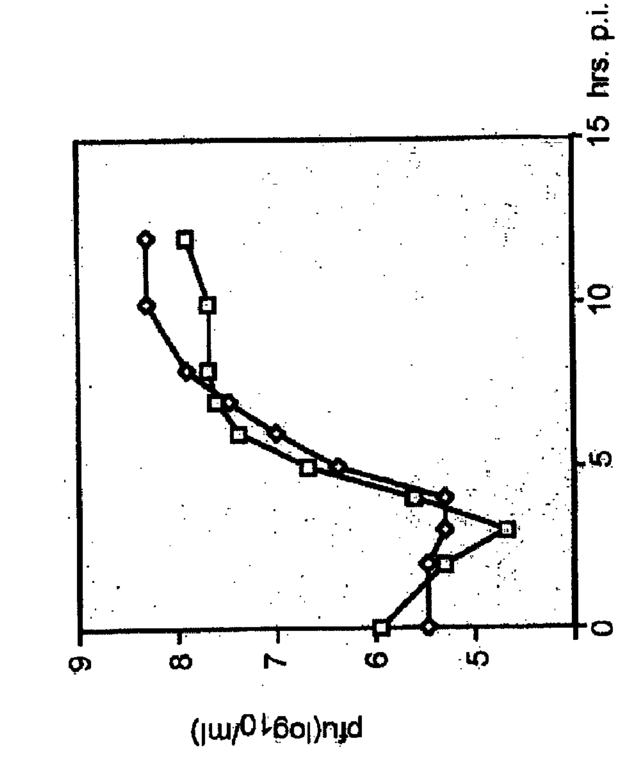

The assumptions were confirmed when the growth kinetics of a prototype stable poliovirus-based expression vector, RPδ6-$HIV_{tat}$(2), were examined and compared the kinetics of viral gene expression and foreign insert expression to RPδ6 (lacking any foreign insert) (FIG. 12). Comparative one-step growth curves of RPδ6-$HIV_{tat}$(2) demonstrated slightly accelerated viral growth compared to its parent RPδ6 (FIG. 12A). Accordingly, viral gene expression of RPδ6-$HIV_{tat}$(2) occurred earlier at higher levels then viral protein synthesis of its parent (FIG. 12B). Most importantly, Western blot analysis of cell lysates with $HIV_{tat}$-specific antibodies revealed expression rates of the foreign insert corresponding to those of cognate viral gene products (FIG. 12B). The data shown demonstrate efficient translation of the fusion-polyprotein containing the foreign ORF and uninhibited proteolytic processing at the artificial $2A^{pro}$, site (no unprocessed precursors of the foreign gene product were detected).

EXAMPLE III

Generation of CAV21 immunization vectors expressing a model HIV-1 immunogen. A CAV21-based vector expressing a model peptide derived from HIV-1 with defined immunogenic properties in mammalian systems can be constructed. A portion of the $3^{rd}$ variable loop of gp120 from HIV-1 strain IIIB (HIV-$V3_{IIIB}$) that contains defined epitopes for stimulation of humoral (Palker et al, Proc. Natl. Acad. Sci. USA 85:1932-1936 (1988)) and CTL responses (Takahashi et al, Proc. Natl. Acad. Sci. USA 85:3105-3109 (1988)) can be used. In numerous investigations, V3 sequences have been shown to potently elicit humoral (Bradney et al, J. Virol. 76:517-527 (2002), Hart et al, J. Immunol. 145:2677-2685 (1990), Palker et al, Proc. Natl. Acad. Sci. USA 85:1932-1936 (1988), Staats et al, J. Immunol. 157:462-472 (1996)) and CTL (Casement et al, Virology 211:261-267 (1995), Hart et al, Proc. Natl. Acad. Sci. USA 88:9448-9452 (1991), Sastry et al, Virology 188:502-509 (1992), Staats et al, J. Immunol. 167:5386-5394 (2001), Takahashi et al, Proc. Natl. Acad. Sci. USA 85:3105-3109 (1988)) responses, both systemically and at mucosal surfaces. In addition, the known MHC I-restricted CTL epitope within HIV-$V3_{IIIB}$ is recognized by H-$2^d$ mice (Takahashi et al, Proc. Natl. Acad. Sci. USA 85:3105-3109 (1988)). Thus, HIV-$V3_{IIIB}$ represents a model immunogen to test features of CAV21-based vaccination vectors: (i) HIV-$V3_{IIIB}$ contains a potent B-cell epitope for raising humoral immunity; (ii) it includes a MHC I-restricted epitope for stimulation of CTL; (iii) it is capable of stimulating immune responses at mucosal surfaces; (iv) its performance in H-$2^d$ BALB/c mice has been verified; (v) there is extensive data on the magnitude of immunity achieved with several methods of administering HIV-$V3_{IIIB}$ to compare with results using CAV21 vectors.

Figure 13:
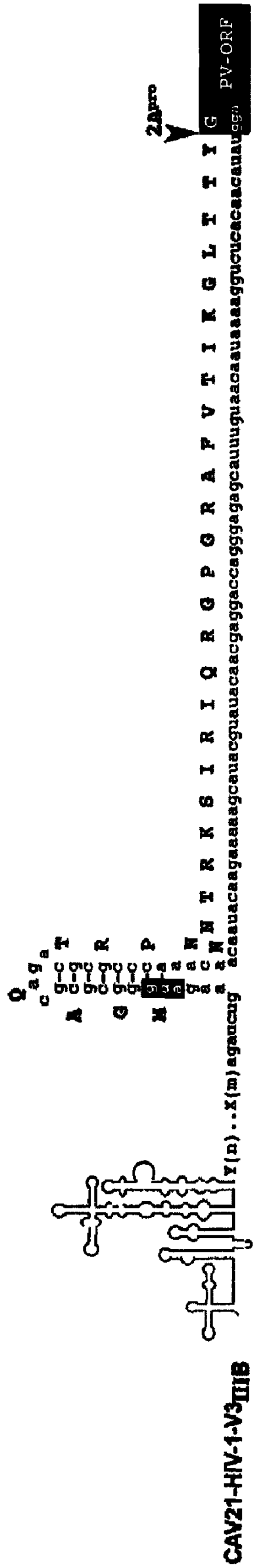
FIG. 13. Genetic structure of the RPδ6-HIV-1($V3_{IIIB}$) expression vector. The nt (SEQ ID NO:22) and aa (SEQ ID NO:23) sequences of the foreign insert are indicated in blue.

Construction of the recombinant CAV21 vector can follow established procedures (Dufresne et al, J. Virol. 76:8966-8972 (2002)); FIG. 13). The coding region for the foreign HIV-$V3_{IIIB}$ peptide (72 nt in total) can be inserted into CAV21 forming a predicted stable SLD VI (FIG. 13). This can be accomplished by silent mutagenesis of the HIV-1 sequences encoding the N-terminal 3 aa of the peptide (FIG. 13). The size of this foreign ORF is well within the range for permanent insert retention in the present vectors. Nevertheless, serial passaging and RT/PCR analyses of the expression vector can be conducted to determine expression levels and insert retention after prolonged passaging. These experiments can be conducted according to well-established procedures (Dufresne et al, J. Virol. 76:8966-8972 (2002)). Monoclonal antibodies recognizing the HIV-V3$_{IIIB}$ are available from the NIH AIDS Research and Reference Reagent Program (catalog number 522; Chesebro and Wehrly, J. Virol. 62:3779-3788 (1988), Pincus et al, J. Immunol. 142:3070-3075 (1989))) for Western blot analyses of HIV-V3$_{IIIB}$ expression. After construction and evaluation in cell culture systems, this vector can be subjected to testing in hICAM-1 tg mice.

Generation of CAV21 immunization vectors expressing poxvirus epitopes. Following the design principles established previously, CAV21-derived immunization vectors expressing poxvirus antigenic material can be generated (FIG. 14). Due to the early establishment of successful prevention and control of poxvirus infection in past centuries, knowledge of the basic mechanisms of orthopoxvirus immunity is fragmentary. As a result, available data on the details of protective immunity from orthopoxvirus infection is limited. It is largely unknown which viral antigens are critical targets for protective immunity and what specific type of immune stimulation is necessary to achieve protection. Most studies published to date have focused on identifying viral antigens capable of raising neutralizing antibodies, although cell-mediated defense mechanisms are likely to play an important role in protection as well. Despite the current paucity of information regarding viral epitopes targeted by the immune system, it seems certain that the renewed interest in poxvirus research and the priority placed on development of new vaccines will lead to the identification of key factors in poxvirus immune protection within the near future. The present platform approach to vaccine design provides the flexibility necessary to quickly take advantage of new discoveries and incorporate requisite antigens into CAV21 vectors as they are identified.

There are two distinct forms of infectious particles produced during orthopoxvirus morphogenesis: intracellular mature virus (IMV) and extracellular enveloped virus (EEV). IMV, consisting of a viral core enclosed within a tightly opposed double membrane, are found in the cytoplasm and represent the bulk of infectious particles produced in an infected cell. Some IMV become wrapped in two additional membranes derived from the trans-Golgi network (Hiller and Weber, J. Virol. 55:651-659 (1985), Schmelz et al, J. Virol. 68:130147 ((1994)) and are transported to the cell surface where fusion of the outermost membrane with the cell membrane facilitates release of the viral particle as EEV. EEV thus retain one additional membrane relative to IMV; this membrane contains several viral proteins absent from IMV. EEV are likely the most important form of the agent for cell to cell and person to person dissemination of virus (Payne, J. Gen. Virol. 50:89-100 (1980)). Since antigens from both forms of virus may contribute to poxvirus immunity, vectors can be designed that encode known neutralizing antibody targets: A27L and B5R, found on IMV and EEV surfaces, respectively.

A27L is a 14 kDa viral membrane protein localized as a trimer on the surface of IMV and infected cells (Rodriguez et al, J. Virol. 61:395-404 (1987), Sodeik et al, J. Virol. 69:3560-3574 (1995)) that has been implicated in fusion with host cells (Gong et al, Virology 178:81-91 (1990), Rodriguez et al, J. Virol. 56:482-488 (1985), Rodriguez et al, J. Virol. 61:395-404 (1987)) and envelopment of EEV (Rodriguez et al, Nucleic Acids Res. 18:53457-5351 (1990)). This factor has also been identified as a target of neutralizing antibodies (Czerny and Mahnel, J. Gen. Virol. 71:2341-2352 (1990), Meyer et al, Virology 200:778-783 (1994)), and animals immunized with purified A27L have shown protection from virulent VACV challenge (Lai et al, J. Virol. 65:5631-5635 (1991)), Ramirez et al, J. Gen. Virol. 83:1059-1067 (2002)). A27L can be included into one of the prototype poxvirus-specific CAV21 immunization vectors (FIG. 14). The ORF (330 nt; Rodriguez and Esteban, J. Virol. 61:3550-3554 (1987)) is near the range of acceptable size for stable insertion into the RPδ6 picornavirus vectors (Dufresne et al, J. Virol. 76:8966-8972 (2002)). It is anticipated that permanent retention of foreign insert can be achieved (insert retention can be considered permanent if full-length foreign ORF persists for at least 20 passages in HeLa cells or, alternatively, in mouse L fibroblasts expressing hICAM-1).

However, should insertion of the entire A27L ORF confer genetic instability, full-length A27L can be substituted with a truncated version (A27L 20) deleted for the C-terminal 20 amino acids (FIG. 14C). This portion of the A27L gene product includes part of an anchoring domain that functions to tether the protein to the IMV envelope through interactions with an interior membrane protein, A17L (Vásquez et al, J. Virol. 72:10126-10137 (1989), Vásquez et al, J. Virol. 73:9098-9101 (1999)). A27L 20 retains functional domains for oligomer formation and neutralization (Gromeier et al, J. virol. 73:958-964 (1998), Takahashi and Ichihashi, Virology 71:1821-1833 (1994), Vásquez et al, J. Virol. 72:10126-10137 (1989)). Therefore, it would not be expected to differ in immunogenicity from A27L. The reduction in coding sequence from 330 to 270 nt would place A27L 20 well within the stable coding capacity of the present vectors (FIG. 14C).

B5R is amongst a set of proteins found uniquely associated with EEV particles. It is a type I membrane glycoprotein with four short consensus repeat (SCR) domains characteristic of cellular complement control factors (Takahashi-Nishimaki et al, J. Cell Biol. 121:521-541 (1991)) and is localized specifically on the outer surface of mature EEV and infected cells (Engelstad and Smith, Virology 194:627-637 (1993), Isaacs et al, J. Virol. 66:7217-7224 (1992)). It influences EEV morphogenesis, normal plaque size, and virulence (Engelstad et al, Virology 188:801-810 (1992), Sanderson et al, J. Gen. Virol. 79:1415-1425 (1998), Wolffe et al, J. Virol. 67:4732-4741 (1993)). B5R is the target of neutralizing antibodies (Czerny and Mahnel, J. Gen. Virol. 71:2341-2352 (1990), Galmiche et al, Virology 254:71-80 (1999), Law and Smith, Virology 280:132-142 (2001)) and it has been demonstrated that B5R immunization can provide protection from vaccinia challenge in correlation with anti-B5R antibody titers (Galmiche et al, Virology 254:71-80 (1999)). B5R represents an attractive target for incorporation into an EEV-specific immunization vector. While the entire B5R ORF may be too large to be accommodated by the present vectors, the neutralization epitopes in B5R have been mapped to SCR 1 (Law and Smith, Virology 280:132-142 (2001)). SCR 1 contains 57 amino acids encoded by 171 nt, an insert size that conforms to the general requirements for use in the present vector platform. A CAV21 vector can be produced encoding SCR 1 from cowpoxvirus (CPV) B5R according to established procedures. (FIG. 14).

Recombinant CAV21 vectors expressing orthopoxvirus antigenic material can be tested by: (i) Western blot assay to ascertain expression of the foreign ORF over serial passages in HeLa cells, (ii) serial passaging and RT/PCR analysis to evaluate genetic stability, and (iii) comparative one-step growth curve analysis in HeLa- and mouse L fibroblasts stably transfected with hICAM-1 cDNA. Vectors thus characterized and determined to permanently retain the foreign insert can be further tested in hICAM-1 tg mice.

All documents cited above are hereby incorporated in their entirety by reference.

What is claimed is:

1. An expression vector comprising an Enterovirus a portion of an internal ribosomal entry site (IRES) of which is replaced by a heterologous sequence encoding a protein,
   wherein a protein-encoding portion of said heterologous sequence replaces stem loop domain VI of said IRES and has the secondary structure, and thereby the function, of said replaced stem loop domain VI of said IRES, and
   wherein said heterologous sequence encoding said protein is up to 300 nucleotides in length.

2. The vector according to claim 1 wherein said Enterovirus is a poliovirus.

3. The vector according to claim 1 wherein said protein encoding portion of said heterologous sequence encodes an antigen.

4. The vector according to claim 3 wherein said antigen is a bacterial, viral or fungal antigen.

5. A method of inducing an immune response in a patient comprising administering to said patient the vector according to claim 3 under conditions such that said protein-encoding portion of said heterologous sequence is expressed and induction of said immune response is effected.

6. The vector according to claim 1 wherein said protein-encoding portion of said heterologous sequence encodes a polypeptide associated with a disease or disorder.

7. A host cell comprising the vector according to claim 1.

8. The cell according to claim 7 wherein said cell is a mammalian cell.

9. A composition comprising the vector according to claim 1 and a carrier.

10. A viral vector obtainable by replacing at least stem-loop domain VI of an IRES of an Enterovirus with a protein encoding portion of a heterologous sequence,
   wherein said protein-encoding portion of said heterologous sequence is a structural and functional mimic of said replaced stem-loop domain VI, and
   wherein said heterologous sequence is up to 300 nucleotides in length.

11. An expression vector comprising RPδ6 and a nucleic acid sequence encoding an antigen operably incorporated therein, wherein said nucleic acid sequence is up to 300 nucleotides in length.

* * * * *

SEQUENCE LISTING

<160> NUMBER OF SEQ ID NOS: 47

<210> SEQ ID NO 1
<211> LENGTH: 10
<212> TYPE: RNA
<213> ORGANISM: Artificial Sequence
<220> FEATURE:
<223> OTHER INFORMATION: Description of Artificial Sequence:Poliovirus

<400> SEQUENCE: 1
uauggagcuc 10

<210> SEQ ID NO 2
<211> LENGTH: 77
<212> TYPE: RNA
<213> ORGANISM: Artificial Sequence
<220> FEATURE:
<223> OTHER INFORMATION: Description of Artificial Sequence:SIV

<400> SEQUENCE: 2
uguuucacuu uuuccuuuau auuugcuuau ggugacaaua uauacauaua uauauuggca 60
ccaugggcgc gcaaaac 77

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence:SIV

<400> SEQUENCE: 3

Met Gly Ala Gln Asn
1 5

<210> SEQ ID NO 4
<211> LENGTH: 54
<212> TYPE: RNA
<213> ORGANISM: Artificial Sequence
<220> FEATURE:
<223> OTHER INFORMATION: Description of Artificial Sequence:SIV

<400> SEQUENCE: 4
uguuucacuu uuuccuuuag aucugaccau gggcgcgcaa aacuccgucu uguc 54

<210> SEQ ID NO 5
<211> LENGTH: 54
<212> TYPE: RNA
<213> ORGANISM: Artificial Sequence
<220> FEATURE:
<223> OTHER INFORMATION: Description of Artificial Sequence:SIV

<400> SEQUENCE: 5
uguuucacuu uuuccuuuag aucugaccau gggcgcgcaa aacuccgucu uguc 54

<210> SEQ ID NO 6
<211> LENGTH: 66
<212> TYPE: RNA
<213> ORGANISM: Artificial Sequence
<220> FEATURE:
<223> OTHER INFORMATION: Description of Artificial Sequence:Poliovirus

<400> SEQUENCE: 6
uuucacuuuc uccuuuauau uugcuuaugg ugacaauaua uacauauaua uauuggcacc 60
auggga 66

<210> SEQ ID NO 7
<211> LENGTH: 32
<212> TYPE: RNA
<213> ORGANISM: Artificial Sequence
<220> FEATURE:
<223> OTHER INFORMATION: Description of Artificial Sequence:Poliovirus

<400> SEQUENCE: 7
uuucacuuuc uccuuuagau cugaccaugg ga 32

<210> SEQ ID NO 8
<211> LENGTH: 42
<212> TYPE: RNA
<213> ORGANISM: Artificial Sequence
<220> FEATURE:
<223> OTHER INFORMATION: Description of Artificial Sequence:FimH

<400> SEQUENCE: 8
agaucugacc augggugcac aguauaaaac cgccaauggu ca 42

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence:FimH

<400> SEQUENCE: 9

Lys Gly Leu Thr Thr Tyr Gly
1 5

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence:FimH

<400> SEQUENCE: 10
aaaggucuca caacauaugg a 21

<210> SEQ ID NO 11
<211> LENGTH: 67
<212> TYPE: RNA
<213> ORGANISM: Artificial Sequence
<220> FEATURE:
<223> OTHER INFORMATION: Description of Artificial Sequence:HIV

<400> SEQUENCE: 11
agaucugacc augggggccc aggagccagu agauccuaga cuaaggcccu ggaagcaccc 60
aggguca 67

<210> SEQ ID NO 12
<211> LENGTH: 35
<212> TYPE: RNA
<213> ORGANISM: Artificial Sequence
<220> FEATURE:
<223> OTHER INFORMATION: Description of Artificial Sequence:SIV

<400> SEQUENCE: 12
agaucugaag augggcgcgc aaaacuccgu cuuac 35

<210> SEQ ID NO 13
<211> LENGTH: 57
<212> TYPE: RNA

-continued

<213> ORGANISM: Artificial Sequence
<220> FEATURE:
<223> OTHER INFORMATION: Description of Artificial Sequence:EGFP

<400> SEQUENCE: 13
agaucugaac augggugcac aggucuccag aggagaggag cuguucaccc agguuca 57

<210> SEQ ID NO 14
<211> LENGTH: 34
<212> TYPE: RNA
<213> ORGANISM: Artificial Sequence
<220> FEATURE:
<223> OTHER INFORMATION: Description of Artificial Sequence:SIV

<400> SEQUENCE: 14
agaucugaag augggcgcgc aaaacuccgu cuua 34

<210> SEQ ID NO 15
<211> LENGTH: 12
<212> TYPE: RNA
<213> ORGANISM: Artificial Sequence
<220> FEATURE:
<223> OTHER INFORMATION: Description of Artificial Sequence:SIV

<400> SEQUENCE: 15
augggcgcgc aa 12

<210> SEQ ID NO 16
<211> LENGTH: 35
<212> TYPE: RNA
<213> ORGANISM: Artificial Sequence
<220> FEATURE:
<223> OTHER INFORMATION: Description of Artificial Sequence:SIV

<400> SEQUENCE: 16
agaucugacc augggcgcgc aaaacuccgu cuuac 35

<210> SEQ ID NO 17
<211> LENGTH: 36
<212> TYPE: RNA
<213> ORGANISM: Artificial Sequence
<220> FEATURE:
<223> OTHER INFORMATION: Description of Artificial Sequence:HIV

<400> SEQUENCE: 17
agaucugacc auggggggccc aagaaccagu cgaucc 36

<210> SEQ ID NO 18
<211> LENGTH: 36
<212> TYPE: RNA
<213> ORGANISM: Artificial Sequence
<220> FEATURE:
<223> OTHER INFORMATION: Description of Artificial Sequence:HIV

<400> SEQUENCE: 18
agaucugaag augggagcac aagaaccagu agaucc 36

<210> SEQ ID NO 19
<211> LENGTH: 28
<212> TYPE: RNA
<213> ORGANISM: Artificial Sequence
<220> FEATURE:
<223> OTHER INFORMATION: Description of Artificial Sequence:HIV

<400> SEQUENCE: 19
agaucugaag augggagcac aagaacca 28

<210> SEQ ID NO 20
<211> LENGTH: 40
<212> TYPE: RNA
<213> ORGANISM: Artificial Sequence
<220> FEATURE:
<223> OTHER INFORMATION: Description of Artificial Sequence:HIV

<400> SEQUENCE: 20
agaucugaag augggagcac aagaaccagu agauccaaga 40

<210> SEQ ID NO 21
<211> LENGTH: 18
<212> TYPE: RNA
<213> ORGANISM: Artificial Sequence
<220> FEATURE:
<223> OTHER INFORMATION: Description of Artificial Sequence:HIV

<400> SEQUENCE: 21
guuuguuuca uaacaaaa 18

<210> SEQ ID NO 22
<211> LENGTH: 115
<212> TYPE: RNA
<213> ORGANISM: Artificial Sequence
<220> FEATURE:
<223> OTHER INFORMATION: Description of Artificial Sequence:HIV

<400> SEQUENCE: 22
agaucugaag augggcgcgc agacgcgccc aaacaacaau acaagaaaaa gcauacguau 60
acaacgagga ccagggagag cauuuguaac aauaaaaggu cucacaacau augga 115

<210> SEQ ID NO 23
<211> LENGTH: 35
<212> TYPE: PRT
<213> ORGANISM: Artificial Sequence
<220> FEATURE:
<223> OTHER INFORMATION: Description of Artificial Sequence:HIV

<400> SEQUENCE: 23

Met Gly Ala Gln Thr Arg Pro Asn Asn Asn Thr Arg Lys Ser Ile Arg
1 5 10 15

Ile Gln Arg Gly Pro Gly Arg Ala Phe Val Thr Ile Lys Gly Leu Thr
20 25 30

Thr Tyr Gly
35

<210> SEQ ID NO 24
<211> LENGTH: 359
<212> TYPE: DNA
<213> ORGANISM: Artificial Sequence
<220> FEATURE:
<223> OTHER INFORMATION: Description of Artificial Sequence:CPV A27L gene

<400> SEQUENCE: 24
gtactttaaa tggacggaac tcttttcccc ggagatgacg atcttgcaat tccagcgact 60
gaatttttct ctacaaaggc tgctaagaag ccagaggcta aacgcgaagc aattgttaaa 120
gctgagggag atgacaatga agaaactctc aaacaacgac taactaattt ggaaaaaaag 180
attactaatg taacaacaaa gtttgaacaa atcgaaaagt gttgtaaacg caacgatgaa 240
gttctattta ggttggaaaa tcatgctgaa actctaagag cggctatgat atctctggct 300
aaaaagattg atgttcagac tggacggcga ccatatgaat aaactcaact cttttgttt 359

<210> SEQ ID NO 25
<211> LENGTH: 25
<212> TYPE: PRT
<213> ORGANISM: Artificial Sequence
<220> FEATURE:
<223> OTHER INFORMATION: Description of Artificial Sequence:CPV

<400> SEQUENCE: 25

```
Met Asp Gly Thr Leu Phe Pro Gly Asp Asp Asp Leu Ala Ile Asp Ala
  1               5                  10                  15

Thr Glu Phe Phe Ser Thr Lys Ala Ala
             20                  25
```

<210> SEQ ID NO 26
<211> LENGTH: 23
<212> TYPE: PRT
<213> ORGANISM: Artificial Sequence
<220> FEATURE:
<223> OTHER INFORMATION: Description of Artificial Sequence:CPV

<400> SEQUENCE: 26

```
Thr Leu Arg Ala Ala Met Ile Ser Leu Ala Lys Lys Ile Asp Val Gln
  1               5                  10                  15

Thr Gly Arg Arg Pro Tyr Glu
             20
```

<210> SEQ ID NO 27
<211> LENGTH: 55
<212> TYPE: RNA
<213> ORGANISM: Artificial Sequence
<220> FEATURE:
<223> OTHER INFORMATION: Description of Artificial Sequence:
      CAV21-CPV-A27L

<400> SEQUENCE: 27

```
agaucugagg augggggccc caggaugggc ccucuucccc ggagaugacg aucuu          55
```

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence:
      CA21-CPV-A27L

<400> SEQUENCE: 28

```
Gly Ala Gln Asp Gly Thr Leu Phe Pro Gly Asp Asp Asp Leu
  1               5                  10
```

<210> SEQ ID NO 29
<211> LENGTH: 30
<212> TYPE: RNA
<213> ORGANISM: Artificial Sequence
<220> FEATURE:
<223> OTHER INFORMATION: Description of Artificial Sequence:
      CAV21-CPV-A27L

<400> SEQUENCE: 29

```
ccauaugaaa aaggucucac aacauaugga                                      30
```

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence:
      CAV21-CPV-A27L -continued

<400> SEQUENCE: 30

Pro Tyr Glu Lys Gly Leu Thr Thr Tyr Gly
1 5 10

<210> SEQ ID NO 31
<211> LENGTH: 30
<212> TYPE: RNA
<213> ORGANISM: Artificial Sequence
<220> FEATURE:
<223> OTHER INFORMATION: Description of Artificial Sequence: CAV21-CPV-A27Ldelta20

<400> SEQUENCE: 31
acucuaagaa aaggucucac aacauaugga 30

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: CAV21-CPV-A27Ldelta20

<400> SEQUENCE: 32

Thr Leu Arg Lys Gly Leu Thr Thr Tyr Gly
1 5 10

<210> SEQ ID NO 33
<211> LENGTH: 300
<212> TYPE: DNA
<213> ORGANISM: Artificial Sequence
<220> FEATURE:
<223> OTHER INFORMATION: Description of Artificial Sequence:CPVB5R

<400> SEQUENCE: 33
aacactcata aataaaaatg aaaacgattt ccgttgttac gttgttatgc gtactacctg 60
ctgttgttta ttcaacatgt actgtaccca ctatgaataa cgctaaatta acgtctaccg 120
aaacatcgtt taatgataaa cagaaagtta cgtttacatg tgatcaggga tatcattctt 180
cggatccaaa tgctgtctgc gaaacagata aatggaaata cgaaaatcca tgcaaaaaaa 240
tgtgcacagt ttctgattac atctctgaat tatataataa accgctatac gaagtgaatt 300

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence:CPVB5R

<400> SEQUENCE: 34

Cys Thr Val Pro Thr Met Asn Asn Ala Lys Leu
1 5 10

<210> SEQ ID NO 35
<211> LENGTH: 56
<212> TYPE: DNA/RNA
<213> ORGANISM: Artificial Sequence
<220> FEATURE:
<223> OTHER INFORMATION: Description of Combined DNA/RNA Molecule: Recombinant CAV21 expression vector
<220> FEATURE:
<223> OTHER INFORMATION: Description of Artificial Sequence: CAV21-CPV-B5R

<400> SEQUENCE: 35
agaucugauc augggcgccc agugcacgga ugcccacgau gaataacgct aaatta 56

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence:
CAV21-CPV-B5R

<400> SEQUENCE: 36

Gly Ala Gln Cys Thr Val Pro Thr Met Asn Asn Ala Lys Leu
1 5 10

<210> SEQ ID NO 37
<211> LENGTH: 30
<212> TYPE: DNA/RNA
<213> ORGANISM: Artificial Sequence
<220> FEATURE:
<223> OTHER INFORMATION: Description of Combined DNA/RNA Molecule:
Recombinant CAV21 expression vector
<220> FEATURE:
<223> OTHER INFORMATION: Description of Artificial Sequence:
CAV21-CPV-B5R

<400> SEQUENCE: 37
aatccatgca aaggucucac aacauaugga 30

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence:
CAV21-CPV-B5R

<400> SEQUENCE: 38

Asn Pro Cys Lys Gly Leu Thr Thr Tyr Gly
1 5 10

<210> SEQ ID NO 39
<211> LENGTH: 66
<212> TYPE: RNA
<213> ORGANISM: Artificial Sequence
<220> FEATURE:
<223> OTHER INFORMATION: Description of Artificial Sequence:Poliovirus

<400> SEQUENCE: 39
uguuucacuu uuuccuuuau auuugcuuau guggacaaua uauacaauau auauauuggc 60
cacaug 66

<210> SEQ ID NO 40
<211> LENGTH: 30
<212> TYPE: RNA
<213> ORGANISM: Artificial Sequence
<220> FEATURE:
<223> OTHER INFORMATION: Description of Artificial Sequence:Poliovirus

<400> SEQUENCE: 40
uguuucacuu uuuccuuuag aucuaccaug 30

<210> SEQ ID NO 41
<211> LENGTH: 100

-continued

<212> TYPE: RNA
<213> ORGANISM: Artificial Sequence
<220> FEATURE:
<223> OTHER INFORMATION: Description of Artificial Sequence:Poliovirus

<400> SEQUENCE: 41
uguuucacuu uuuccuuuag aucugaccau gggcgcgcag uguaaaaccg ccaaugguac 60
cgcuaucccu auuggcggug gcagcgccaa uguuuaugua 100

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence:Poliovirus

<400> SEQUENCE: 42

Gly Leu Thr Thr Tyr Gly
1 5

<210> SEQ ID NO 43
<211> LENGTH: 22
<212> TYPE: RNA
<213> ORGANISM: Artificial Sequence
<220> FEATURE:
<223> OTHER INFORMATION: Description of Artificial Sequence:Poliovirus

<400> SEQUENCE: 43
ggucucacaa cauauggagc uc 22

<210> SEQ ID NO 44
<211> LENGTH: 31
<212> TYPE: RNA
<213> ORGANISM: Artificial Sequence
<220> FEATURE:
<223> OTHER INFORMATION: Description of Artificial Sequence:SIV

<400> SEQUENCE: 44
gggagauggg cgugagaaac uccgucuugu c 31

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence:SIV

<400> SEQUENCE: 45

Met Gly Val Arg Asn Ser Val Leu
1 5

<210> SEQ ID NO 46
<211> LENGTH: 54
<212> TYPE: RNA
<213> ORGANISM: Artificial Sequence
<220> FEATURE:
<223> OTHER INFORMATION: Description of Artificial Sequence:SIV

<400> SEQUENCE: 46
uguuucacuu uuuccuuuag aucugaagau gggcgcgcaa aacuccgucu uguc 54

<210> SEQ ID NO 47
<211> LENGTH: 8
<212> TYPE: PRT

-continued

```
<213> ORGANISM: Artificial Sequence
<220> FEATURE:
<223> OTHER INFORMATION: Description of Artificial Sequence:SIV

<400> SEQUENCE: 47

Met Gly Ala Gln Asn Ser Val Leu
  1             5
```